US011839630B2

(12) United States Patent
Ferrand et al.

(10) Patent No.: US 11,839,630 B2
(45) Date of Patent: Dec. 12, 2023

(54) CAR-T CELLS TARGETING IL-1RAP AND THEIR USE

(71) Applicants: ETABLISSEMENT FRANCAIS DU SANG, La Plaine Saint Denis (FR); INSTITUT NATIONAL DE LA SANTE ET DE LA RECHERCHE MEDICALE (INSERM), Paris (FR); CENTRE HOSPITALIER UNIVERSITAIRE DE BESANCON, Besançon (FR); UNIVERSITE DE FRANCHE COMTE, Besancon (FR)

(72) Inventors: Christophe Ferrand, Dampierre (FR); Marina Deschamps, Antorpe (FR); Fabrice Larosa, Velars sur Ouche (FR)

(73) Assignees: ETABLISSEMENT FRANCAIS DU SANG, La Plaine Saint Denis (FR); INSTITUT NATIONAL DE LA SANTE ET DE LA RECHERCHE, Paris (FR); CENTRE HOSPITALIER UNIVERSITAIRE DE BESANCON, Besancon (FR); UNIVERSITE DE FRANCHE COMTE, Besancon (FR)

( * ) Notice: Subject to any disclaimer, the term of this patent is extended or adjusted under 35 U.S.C. 154(b) by 401 days.

(21) Appl. No.: 16/766,222

(22) PCT Filed: Nov. 14, 2018

(86) PCT No.: PCT/EP2018/081273
§ 371 (c)(1),
(2) Date: May 21, 2020

(87) PCT Pub. No.: WO2019/101604
PCT Pub. Date: May 31, 2019

(65) Prior Publication Data
US 2021/0008108 A1   Jan. 14, 2021

(30) Foreign Application Priority Data

Nov. 23, 2017 (EP) .................................... 17306630

(51) Int. Cl.
| | |
|---|---|
| *C12N 5/10* | (2006.01) |
| *A61K 35/17* | (2015.01) |
| *A61P 35/02* | (2006.01) |
| *C07K 14/725* | (2006.01) |
| *C07K 14/705* | (2006.01) |
| *C07K 14/715* | (2006.01) |
| *C07K 16/28* | (2006.01) |
| *C12N 15/85* | (2006.01) |

(52) U.S. Cl.
CPC .............. *A61K 35/17* (2013.01); *A61P 35/02* (2018.01); *C07K 14/7051* (2013.01); *C07K 14/70517* (2013.01); *C07K 14/70521* (2013.01); *C07K 14/70575* (2013.01); *C07K 14/70578* (2013.01); *C07K 14/7155* (2013.01); *C07K 16/2866* (2013.01); *C12N 5/10* (2013.01); *C12N 15/85* (2013.01); *C07K 2317/565* (2013.01); *C07K 2317/622* (2013.01); *C07K 2319/03* (2013.01); *C07K 2319/33* (2013.01)

(58) Field of Classification Search
CPC . C07K 2317/60; C07K 2317/565; C12N 5/10
USPC ........................................... 424/133.1, 144.1
See application file for complete search history.

(56) References Cited

U.S. PATENT DOCUMENTS

2022/0235138 A1*  7/2022  Deschamps ............ C07K 16/24

FOREIGN PATENT DOCUMENTS

| CN | 106831998 A | 6/2017 |
|---|---|---|
| JP | 2021503952 | * 11/2018 |

OTHER PUBLICATIONS

Trad et al (Journal for ImmunoTherapy of Cancer 2022;10:e004222 (pp. 1-14)).*
Warda et al (Cancer Res Feb. 1, 2019;79(3):663-675. Epub Dec. 4, 2018).*
Warda et al (Cancer Gene Therapy (2021) 28:1365-1375).*
Lippow et al., "Computational design of antibody-affinity improvement beyond in vivo maturation," Nature Biotechnology, 25(10):1171-1176 (2007).*
Sulea et al., "Application of Assisted Design of Antibody and Protein Therapeutics (ADAPT) improves efficacy of a Clostridium difficile toxin A single-domain antibody," Scientific Reports, 8(260):1-11 (2018).*
Hasegawa et al., "Single amino acid substitution in LC-CDR1 induces Russell body phenotype that attenuates cellular protein synthesis through eIF2a phosphorylation and thereby downregulates IgG secretion despite operational secretory pathway traffic," MABS, vol. 9, No. 5, pp. 854-873 (2017).*
Altshuler et al., "Generation of Recombinant Antibodies and Means for Increasing Their Affinity," Biochemistry (Moscow), 75(13):1584-1605 (2010).*
Vajda et al., "Progress toward improved understanding of antibody maturation," Current Opinion in Structural Biology, 67 pp. 226-231 (2021).*

(Continued)

*Primary Examiner* — Lynn A Bristol
(74) *Attorney, Agent, or Firm* — STERNE, KESSLER, GOLDSTEIN & FOX P.L.L.C.

(57) ABSTRACT

The present invention is relative to an isolated nucleic acid molecule encoding a chimeric antigen receptor (CAR), wherein the CAR comprises an antibody or antibody fragment which includes a anti-IL-1RAP binding domain, polypeptides encoded by this nucleic acid molecule, isolated chimeric antigen receptor (CAR) molecule comprising such an antibody or antibody fragment, a vector comprising a nucleic acid molecule encoding a CAR, as well as a T cell comprising this vector. The present invention is also relative to the use of this T cell (autologous or allogeneic) expressing a CAR molecule to treat a proliferative disease in a mammal.

17 Claims, 30 Drawing Sheets

Specification includes a Sequence Listing.

(56) References Cited

OTHER PUBLICATIONS

Marks et al., "How repertoire data are changing antibody science," J. Biol. Chem. 295(29) 9823-9837 (2020).*
Akbar et al., Cell Reports 34, 108856, Mar. 16, 2021).*
Lo et al., "Conformational epitope matching and prediction based on protein surface spiral features," BMC Genomics vol. 22, Article No. 116 (2021).*
Ferrand et al (Vox Sanguinis, (Jun. 2019) vol. 114, Supp. Supplement 1, pp. 6. Abstract No. 1B-02-02. Meeting Info: 29th Regional Congress of the ISBT. Basel, Switzerland. Jun. 22, 2019-Jun. 26, 2019).*
International Search Report and Written Opinion dated Apr. 12, 2019, International Application No. PCT/EP2018/081273, pp. 1-10.
Stuart Rudikoff et al., "Single amino acid substitution altering antigen-binding specificity", Proceedings of National Academy of Sciences USA, vol. 79, Mar. 1982, pp. 1979-1983.
Ling-Ling Yin et al., "Cloning of Vh and Vl Gene of Human anti-IL1RAP McAb and Constructions of Recombinant Chimeric Receptor", Journal of Experimental Hematology, 23(5), 2015, pp. 1272-1276.

\* cited by examiner

100μm

FIGURE 11
A
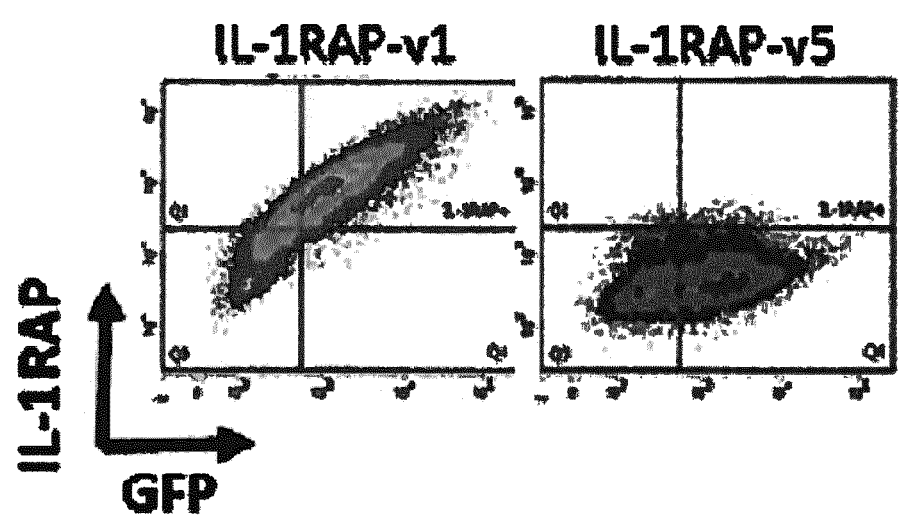
B
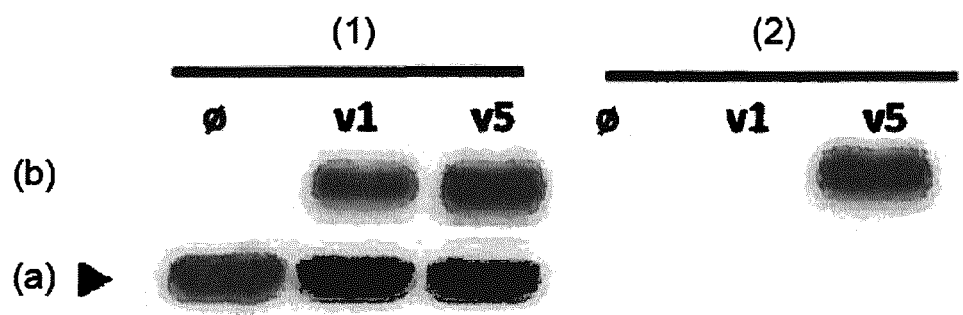

FIGURE 17
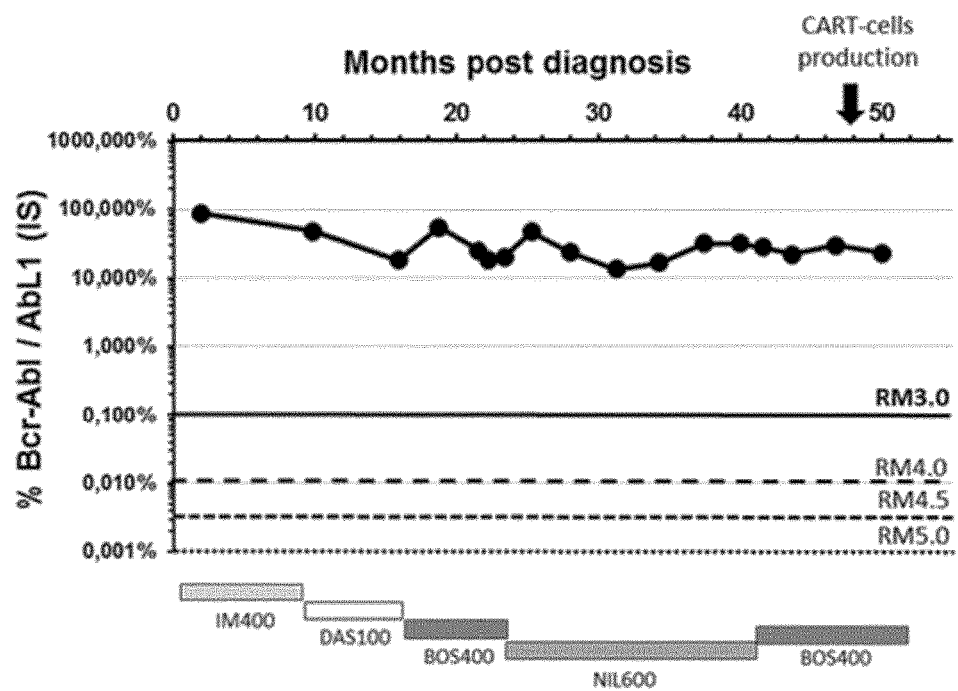
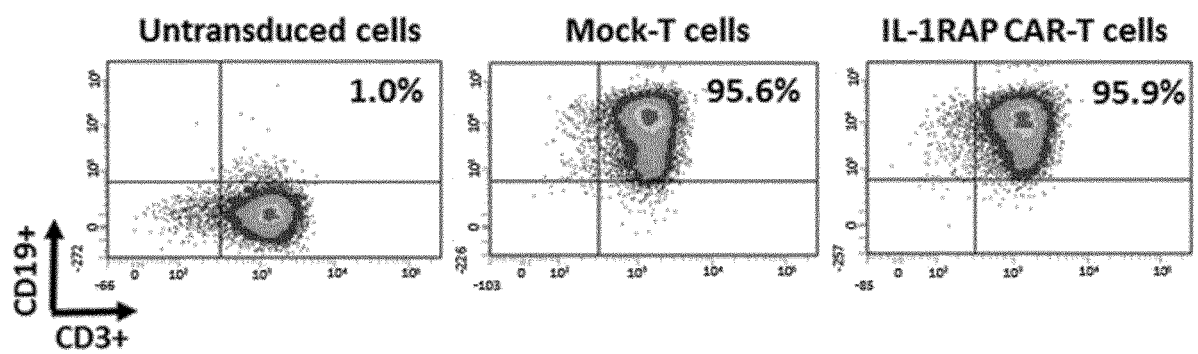

| Patients | Sequence treatment; [Current Treatment] | BCR/ABL (IS) | Time post diagnosis [Months] | Cryopreserved CML PBSC autograft [year; N2 storage] | Transduction efficiency [%] | CD34+ / IL-1RAP+ killing efficiency |
|---|---|---|---|---|---|---|
| CML#1 | IFNγ-IM-DAS; [NIL] | 34% | 258 | 1997; 21y | 92% | 67.38 |
| CML#2 | IM; [Ø] | 0,0011% | 194 | 2002; 16y | 80.9% | 84.41% |
| CML#3 | INFγ-IM,-NIL-DAS-PON-BOS; [IM] | 0,67% | 324 | 2000; 18y | 83.1% | 87.12% |

Ø: treatment free; IFNγ: Interferonγ; IM : Imatinib; DAS : Dasatinib; NIL : Nilotinib; PON : Ponatinib; BOS : Bosutinib

FIGURE 21

Figure 23A:
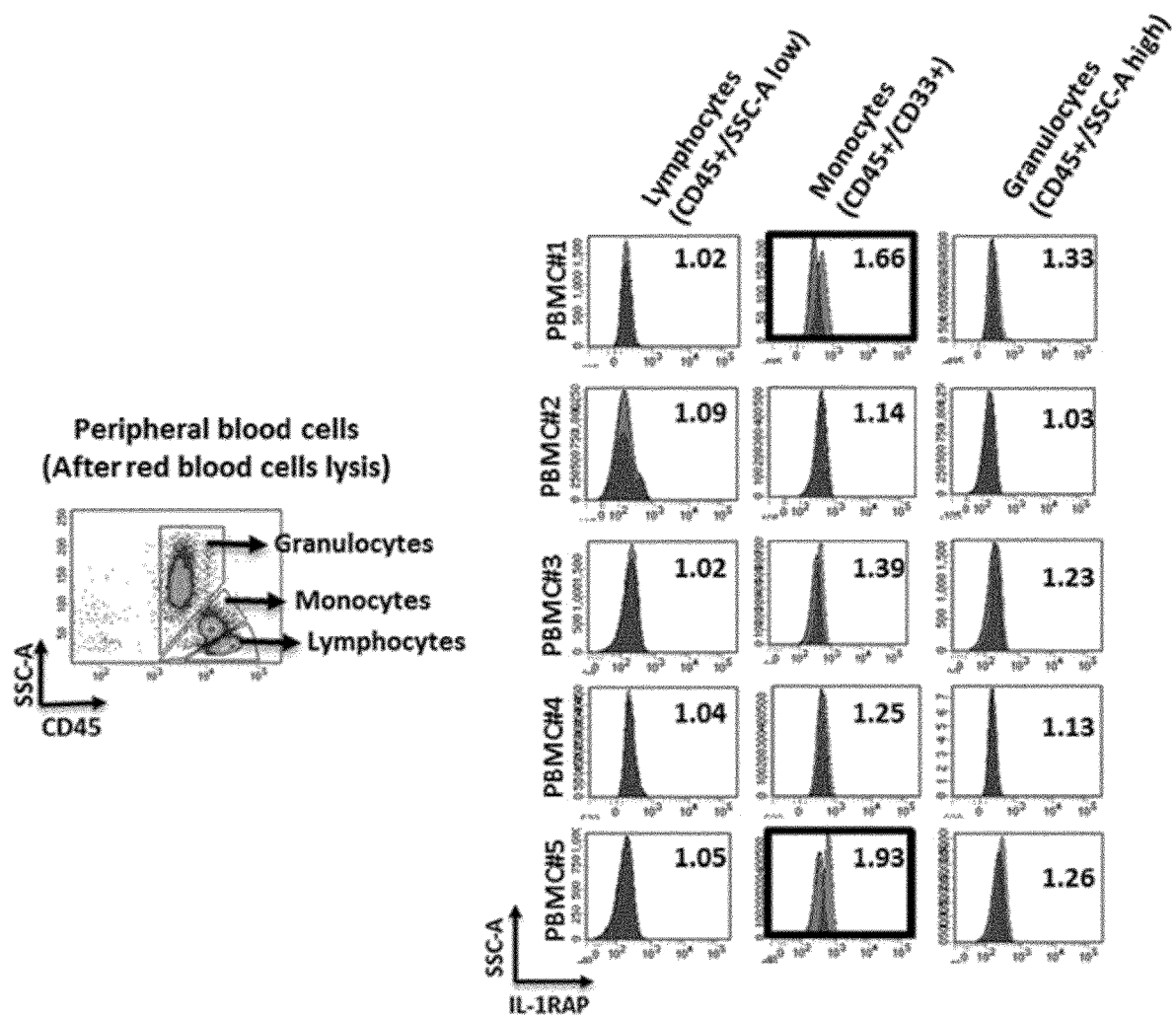
Figure 23B:
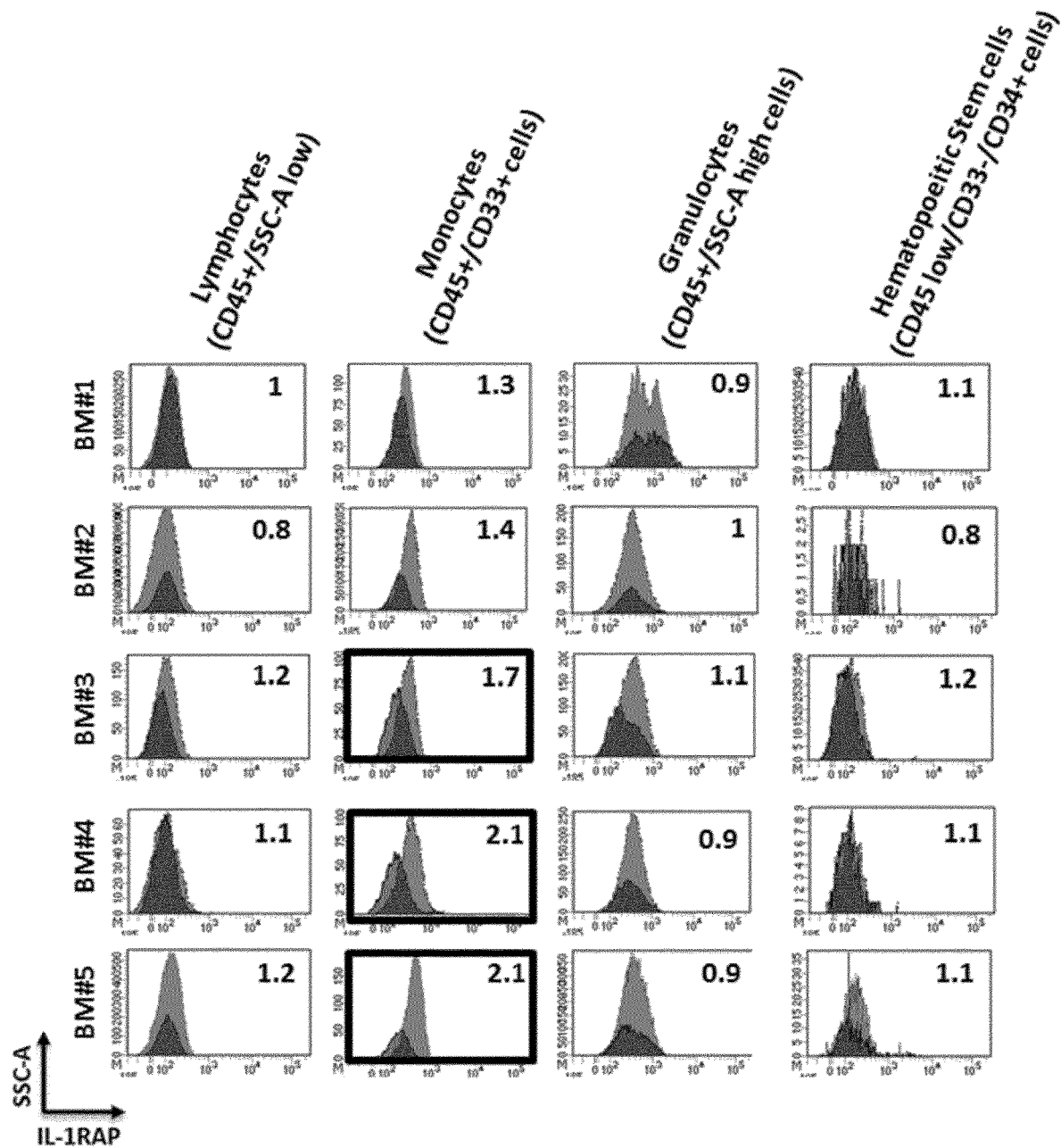
Figure 23C:
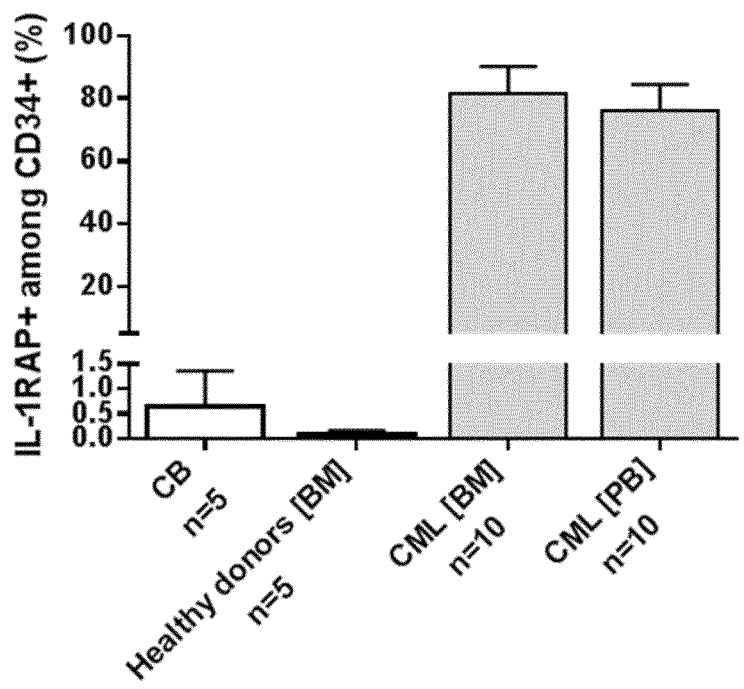
Figure 23D:
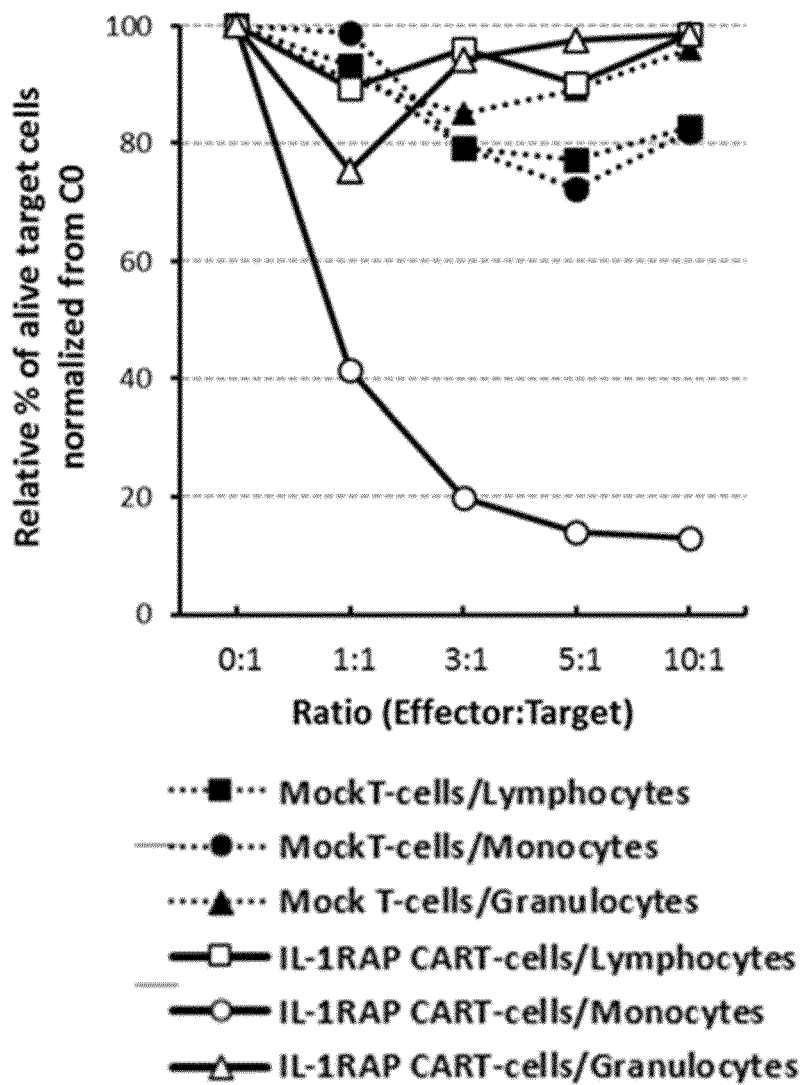

FIGURE 23B (CONTINUATION)
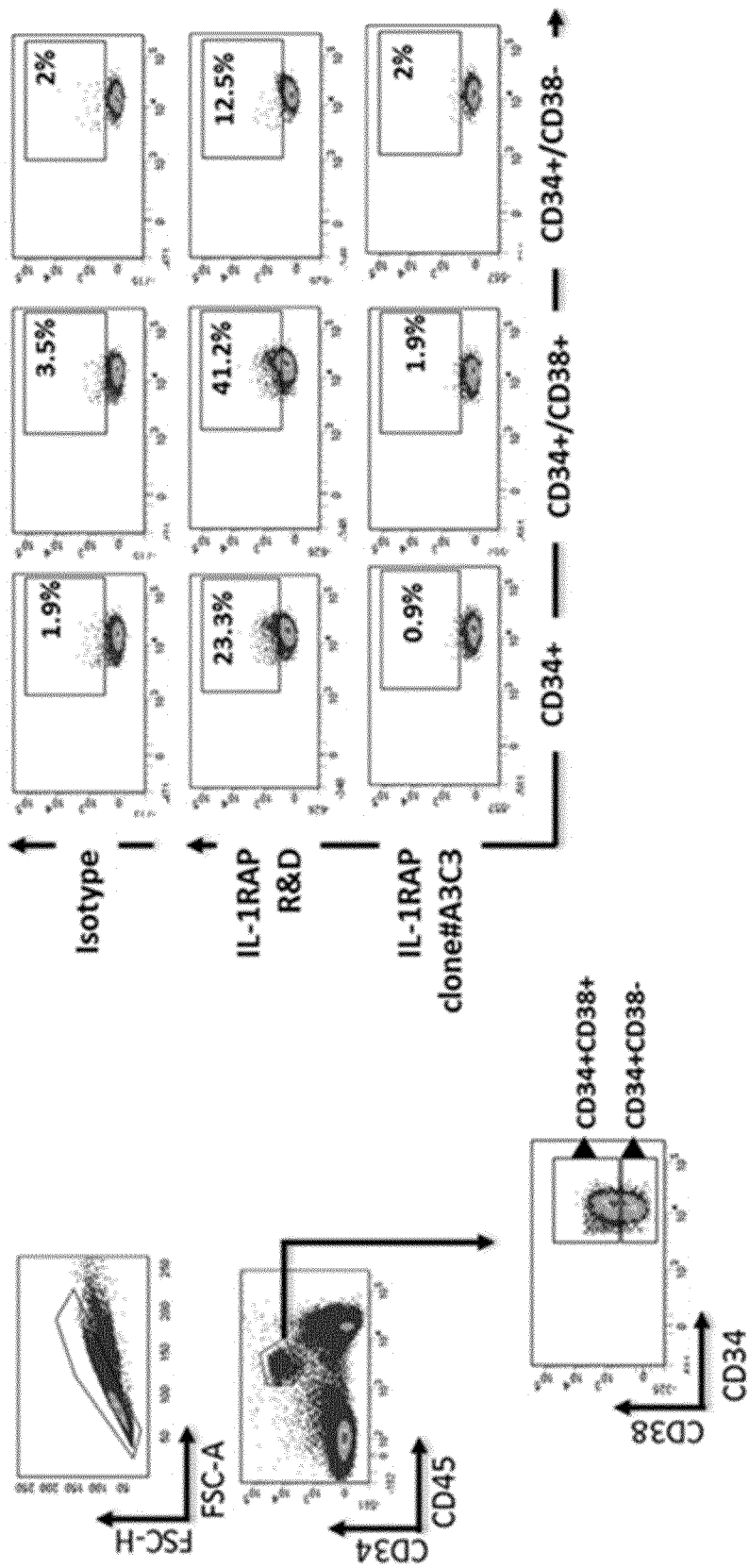

\*\* : $p<0,01$

CAR-T CELLS TARGETING IL-1RAP AND THEIR USE

CROSS-REFERENCE TO RELATED APPLICATIONS

This application is a U.S. National Stage Application of International Application No. PCT/EP2018/081273, filed on Nov. 14, 2018, which claims priority to European Patent Application No. 17306630.9, filed on Nov. 23, 2017, the entire disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on May 20, 2020, is named 1H318460_0004_PCT_ST25.txt and is 10 kilobytes in size.

The present invention is relative to an isolated nucleic acid molecule encoding a chimeric antigen receptor (CAR), wherein the CAR comprises an antibody or antibody fragment which includes a humanized anti-IL-1RAP binding domain, a transmembrane domain, and an intracellular signaling domain comprising at least a stimulatory domain, polypeptides encoded by this nucleic acid molecule and isolated chimeric antigen receptor (CAR) molecules comprising such an antibody or antibody fragment.

The present invention is also relative to a vector comprising a nucleic acid molecule encoding a CAR, as well as a T cell comprising this vector.

The present invention is also relative to the use of this T cell expressing a CAR molecule to treat a proliferative disease in a mammal.

Chronic myelogenous leukemia (CML), also known as chronic myeloid leukemia, is a myeloproliferative disorder characterized by increased proliferation of the granulocytic cell line without the loss of its capacity to differentiate.

CML is a disease of haemopoietic stem cells, arising from a translocation of t(9;22)(q34;q11), with the shortened chromosome 22, designated as Philadelphia chromosome, 22q−. The translocation leads to a juxtaposition of the ABL1 gene from chromosome 9 and the BCR gene from chromosome 22, resulting in a BCR-ABL1 fusion gene that codes for BCR-ABL1 transcripts and fusion proteins with high tyrosine kinase activity. If the molecular pathogenesis of CML is well understood, the mechanism that leads to the gene translocation is unknown.

The incidence of CML ranges between 10 and 15 cases/ $10^6$/year without any major geographic or ethnic differences. The median age at diagnosis ranges between 60 and 65 years in Europe, but is considerably lower in countries with a younger population. CML in children is rare.

Diagnosis of CML is generally straightforward. In most cases, the diagnosis can be made on the basis of a characteristic blood count. Confirmation of diagnosis is obtained by the identification of the Philadelphia chromosome, 22q− or BCR-ABL1 transcripts, or both, in peripheral blood or bone marrow cells.

Before the early 2000s, interferon alpha (IFNα) and hematopoietic stem cell transplantation were the only effective treatments in CML. Hematopoietic stem cell allogeneic graft was considered to be the only potentially curative treatment for eligible patients when a compatible HLA donor was available. This allogeneic graft is an adoptive immunotherapy approach used in the treatment of the majority of aggressive hemopathies. The principle is an immunity transfer that relies on the activity of cytotoxic T effectors through a specific T-receptor. The cytotoxic activity specific to these lymphocytes is, however, restricted by the presentation of the tumor antigens with the molecules of the human leukocyte antigen (HLA) system. The mortality of this type of transplant procedure and the risks of relapse after allograft remain the major stakes of this immunotherapy.

It is well known that graft-versus-leukemia, immunological effect of allogenic stem cell transplantation, as well as efficacy of donor lymphocytes infusion (DLI), remain the only therapy that allow to achieve durable disease remission, if not cured, despite transplant-related mortality toxicities.

Since the early 2000s, the discovery and widespread use of tyrosine kinase inhibitors (TKIs) in the treatment of chronic phase CML has considerably altered the prognosis of this hemopathy with the achievement of survival of more than 90%. The indications of allograft of hematopoietic stem cell in the CML are now reserved for patients intolerant/resistant to TKIs and advanced phases of CML (accelerated or blastic phase).

In 2017, for first-line therapy, the treatment of choice remains the use of tyrosine kinase inhibitors (TKI), although other therapeutic alternatives may be used. On TKI therapy, most patients restore normal haematopoiesis. However, although TKIs like Imatinib, Dasatinib, Nilotinib, Bosutinib or Ponatinib have offered much in terms of overall survival and quality of life for patients with CML, the ability of these agents to cure CML is limited.

Moreover, considerations as intolerance and toxicities, potential risk for pregnancy, or health funding agencies medico-economical purposes lead to consider TKIs discontinuation.

In a multicentre Imatinib study, imatinib treatment (of more than 2 years duration) was discontinued in patients with CML who had molecularly undetectable leukemia. On 69 patients enrolled, forty-two (61%) of these 69 patients relapsed. At 12 months, the probability of persistent molecularly undetectable leukemia for these 69 patients was 41%. This failure results from the inability of TKIs' to eradicate quiescent CML stem cells.

The French study STIM 1 (n=100 patients) that studies attempts to stop Imatinib in patients with complete molecular response has recently been updated in 2017. The rate of molecular relapse after stopping TKI is of 61% in a median time of 2.5 months demonstrating the persistence of the medullary reservoir of the disease in these relapsed patients.

Indeed, current TKIs are more a suppressive rather than a curative therapy, requiring continuous long term administration of TKIs, with potential occurrence of unexpected and unknown adverse events. Moreover, long term TKIs administration for young CML patients may constitute a challenge for the future.

Thus, persisting TKIs resistant CML quiescent precursors need to be eliminated. Genetic approaches offer a potential means to enhance immune recognition and elimination of cancer cells. One promising strategy is to genetically engineer immune effector cells to express chimeric antigen receptors that redirect cytotoxicity toward tumor cells.

Recently, the latest generation of CAR (chimeric antigen receptor)—T cells are emerging, thanks to advances in cellular engineering that make it possible to bypass the mechanisms of tumor escapes. CAR-T cells are T lymphocytes that express a chimeric TCR composed of a constant portion of TCR fused with an immunoglobulin variable fragment. The recognition of the target is unrestricted by the HLA and therefore allows to target all kinds of tumor markers.

Among new immunotherapies, these CAR-T cells directed against a cell surface tumor associated antigen have shown unexpected success in refractory/relapse ALL (acute lymphoid leukemia) (CD19) or CLL (chronic lymphocytic leukemia) (CD19) patients, but also in solid tumors and in preclinical studies in the field of hematology, mainly in MM (multiple myeloma) (CD38, BCMA (B cell maturation antigen), CD44v6 or CS1), AML (acute myelogenous leukemia)) (CD33 or CD123), T cells malignancies (CD5) or lymphomas (CD30).

In CML, gene expression profiling studies have revealed a cell surface biomarker (IL-1RAP or IL-1R3) that is expressed by the leukemic, but not the normal $CD34^+$/$CD38^-$ hematopoietic stem cells. Moreover, IL-1RAP expression is correlated with the tumor burden as well as clinical phase of the CML disease.

IL-1RAP (interleukin-1 receptor accessory protein, Genbank accession No. AAB4059) is a co-receptor of the IL-1 and IL33 receptor, involved in IL-1 signaling, that activates different signaling pathways, including MAP Kinase, p38, NF-κB and others genes implied in inflammation and proliferation. This protein is expressed at the tumor cell surface. IL-1RAP is a thus a promising tumor-associated antigen.

The applicant has discovered that, by using this IL-1RAP antigen, it is possible to generate genetically modified CAR T cells, to be administered to a patient having a cancer or tumor, in particular CML.

The development of a cellular CAR-T targeting the hematopoietic stem cell Phi+, which is the cause of the CML, with the target IL-1RAP, is a means of eradicating the source of hemopathy in addition to or instead of the TKIs which essentially target the precursors of hemopathies.

This new therapeutic weapon can be applied
- to patients who relapse after TKI discontinuation,
- to patients who relapsed post-allograft (graft-versus-leukemia, allogenic stem cell transplantation, donor lymphocytes infusion (DLI)),
- to non-eligible patients with a suboptimal response under TKI or
- to patients presenting an accelerated CML/blast with a major risk of relapse,
- to young or pediatric CML patients.

In one embodiment, a polynucleotide encoding a CAR, the CAR comprising an extracellular domain that binds a target antigen, a transmembrane domain, and one or more intracellular signaling domains is provided. In one embodiment, a T cell genetically modified with a vector comprising a CAR is contemplated herein. T cells expressing a CAR are referred to herein as CAR T cells or CAR modified T cells.

The present invention contemplates, in particular embodiments, cells genetically modified to express the CARs contemplated herein, for use in the treatment of cancers. As used herein, the term "genetically engineered" or "genetically modified" refers to the addition of extra genetic material in the form of DNA or RNA into the total genetic material in a cell.

The terms "#E3C3" and "#A3C3" are understood to be identical: #E3C3 being able to be freely used to refer to #A3C3 and vice versa.

Figure 1:
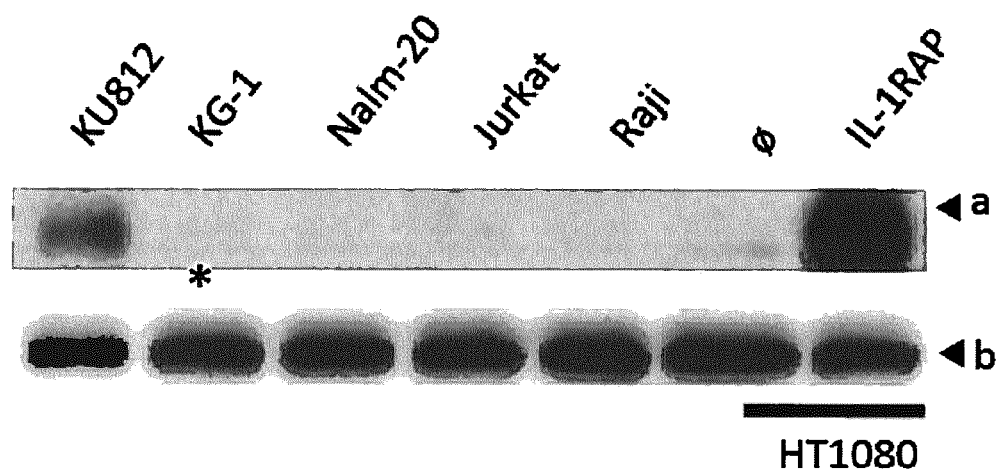

Other objects, features, aspects and advantages of the invention will appear more clearly on reading the description, figures and examples that follow:

FIG. 1: Use of #E3C3 mAb in western blot. The leukemic cell lines KU812, KG-1, Nalm-20, Jurkat, and Raji are used. Transfected HT1080 cell line with IL-1RAP cDNA variant was used as control. Actin was revealed as a protein loading control. Line a: detection of IL-1RAP (72 kDA), Line b: detection of the control actin (43 kDA), *: weak signal.

Figure 2:
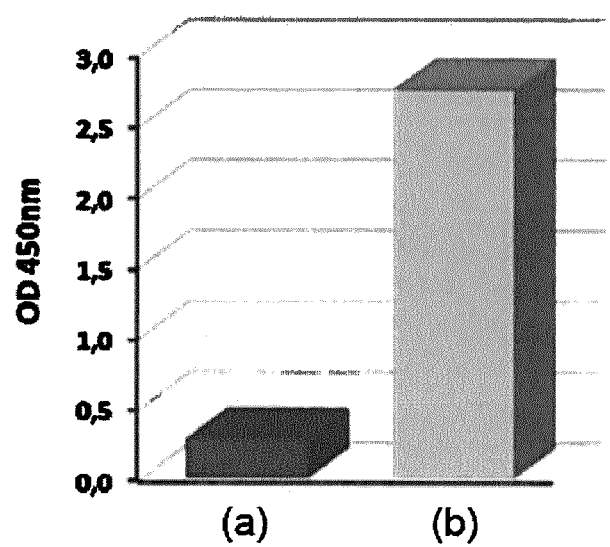

FIG. 2: recognition of IL-1RAP recombinant protein with #E3C3 mAb by the ELISA technique (b). BSA is the negative control (a).

Figure 3:
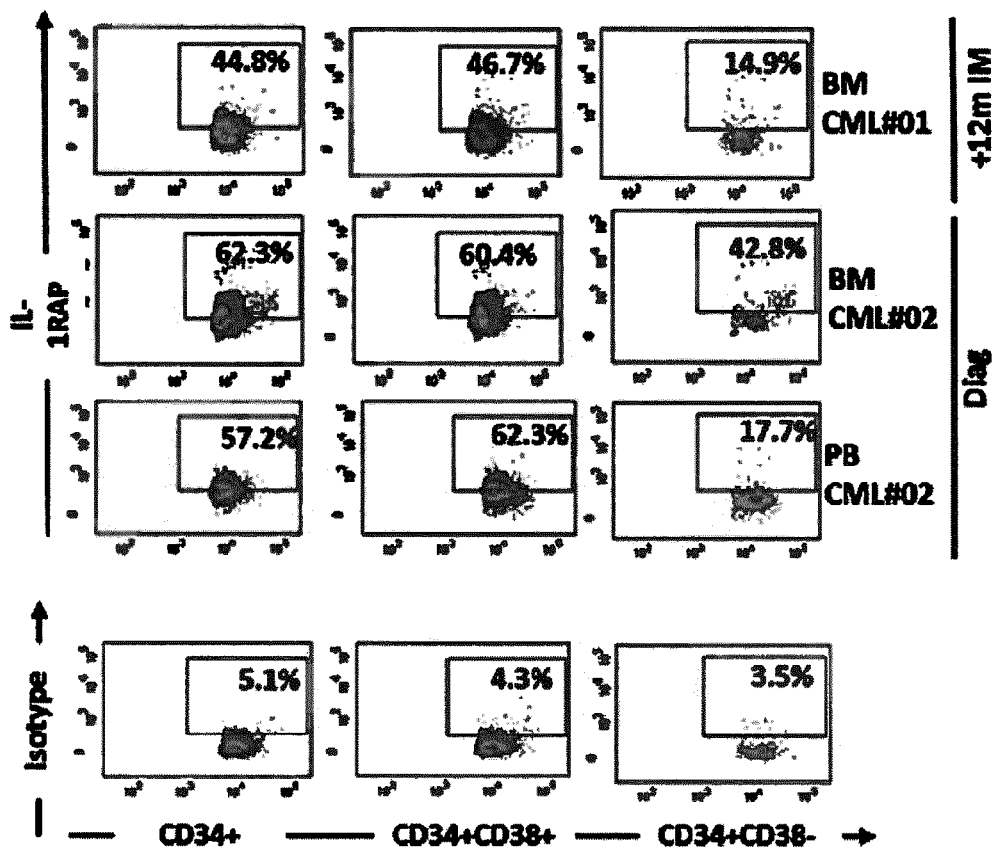

FIG. 3: Immunophenotyping on peripheral blood (PM) or bone marrow (BM) of 2 CML positive patients at diagnosis (Diag) or after Imatinib (IM) treatment. IL-1RAP (#E3C3) was used in combination with CD34+ and CD38– fluorescent staining. Fluorochrome-conjugated isotype control mAbs from the different mAbs were systematically used.

Figure 4:
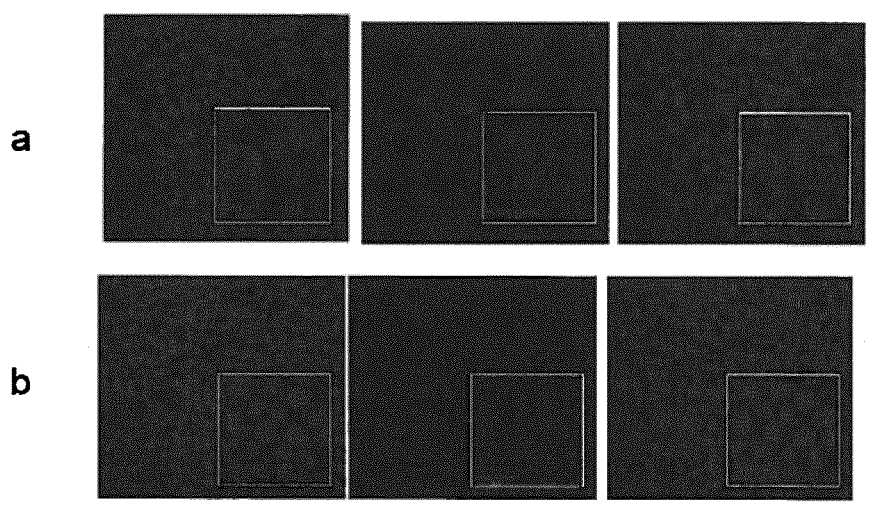

FIG. 4: KU812 (a) and Raji cells lines (b) stained with Fluorescence mAbs [(left panel: anti murine Fc-IgG; medium panel: IL-1RAP (#E3C3)]. Counterstaining was performed by nuclear stain DAPI and superposed to Fluorescent staining (right panel, merge).

Figure 5:
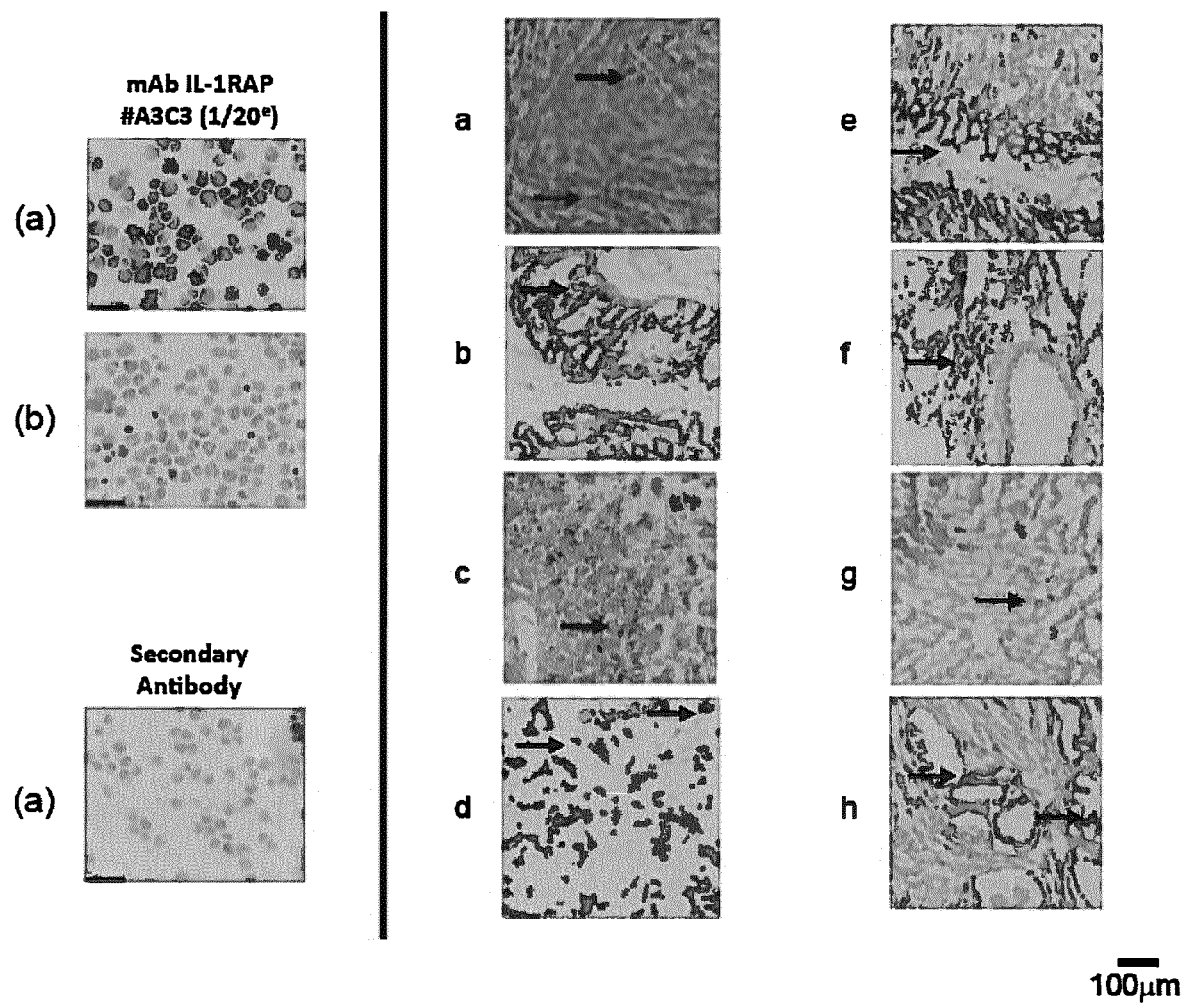

FIG. 5: Specific tissue binding using frozen tissue array. High IL-1RAP (KU812) (a) or negative (Raji) (b) expressing cell lines were respectively used as positive or negative controls. The following tissues have been tested a: Lymph node, b: colon, c: small intestine, d: placenta, e: stomach f: lung, g: spleen and h: prostate.

Figure 6:
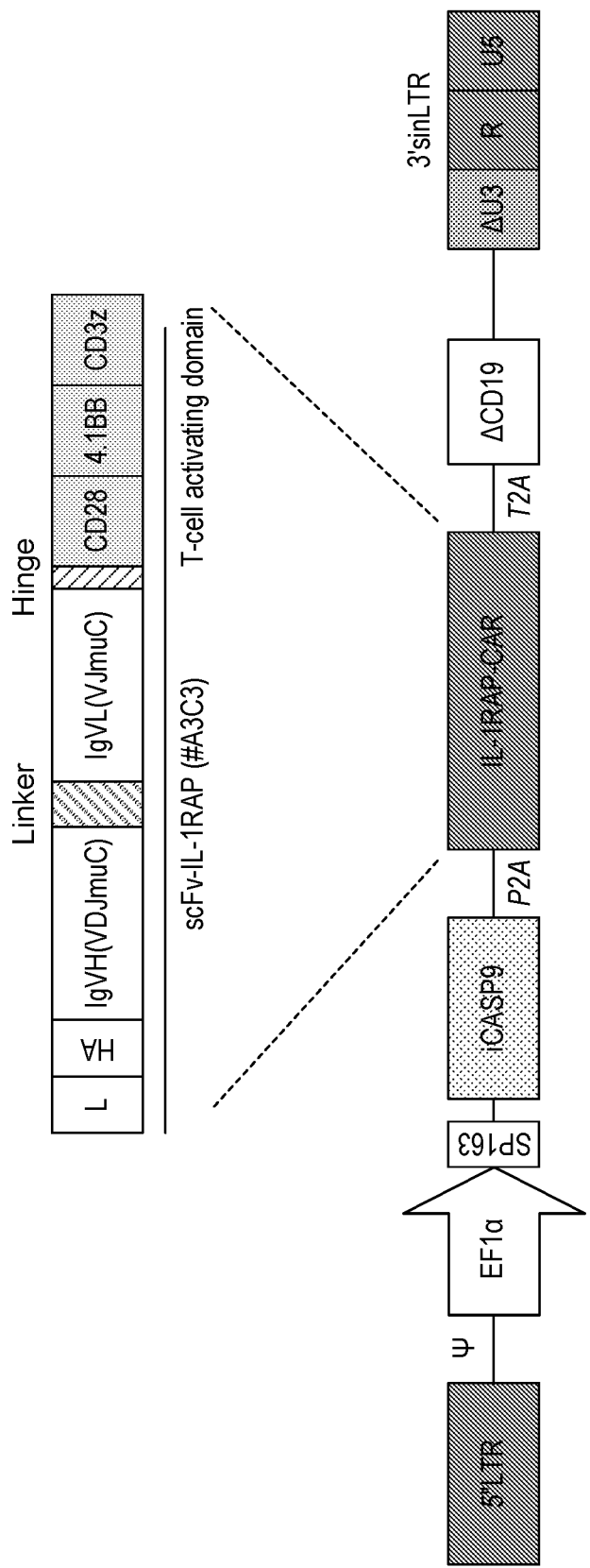

FIG. 6: Design of a SIN lentiviral construct carrying a safety cassette iCASP9, the single chain fragment variable (scFv) of #E3C3 mAb and a cell surface expressed markerΔCD19. The 3 transgenes are separated by 2A peptide cleavage sequences and under control of EF1 promoter plus SP163 enhancer sequence.

Figure 7:
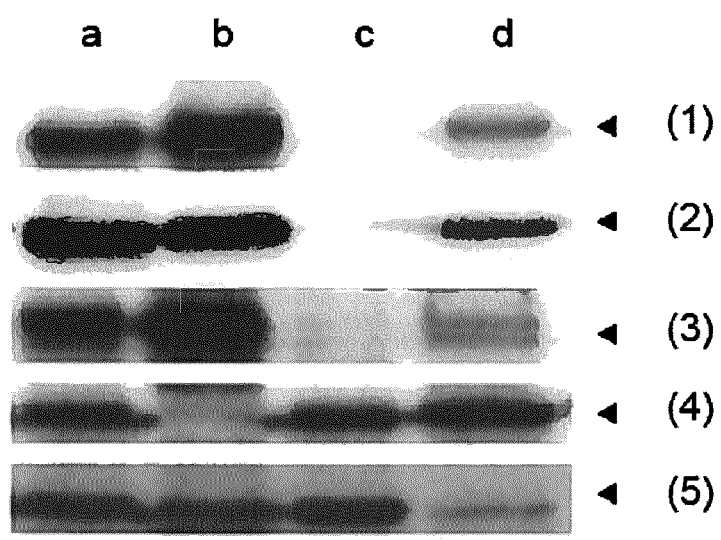

FIG. 7: Western blotting on subcellular fractions of IL-1RAP transduced T cells. a: total lysate, b: membrane, c: cytoplasm, d: nucleus, (1) CAR associated CD3zeta (55 kDa), (2) endogenous CD3zeta (16 kDa), (3) CD45 (147 kDa), (4) lamin (68 kDa), (5) GAPDH (35 kDa).

Figure 8:
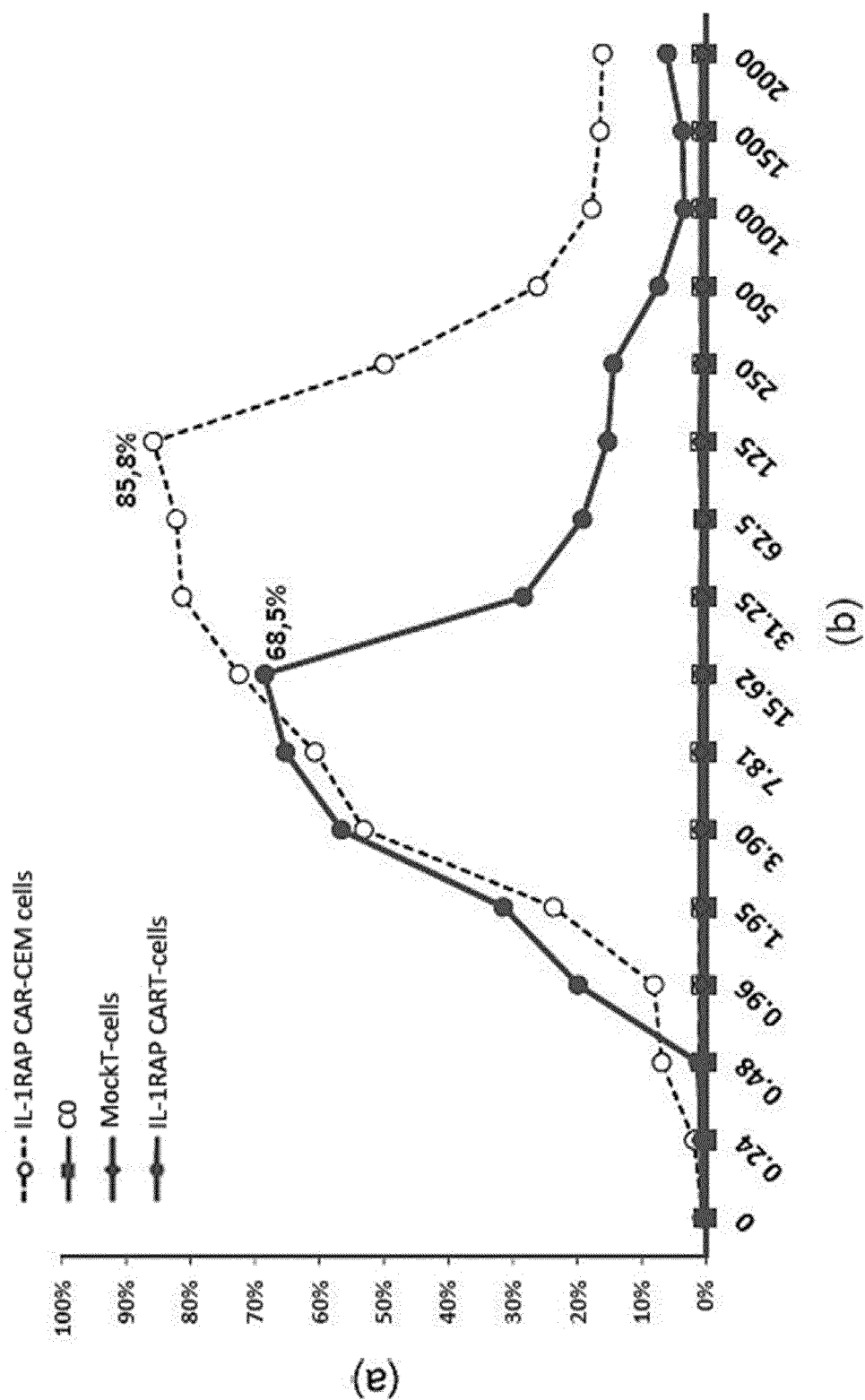

FIG. 8: FACS analysis detection of either IL-1RAP CAR transduced CEM T cell line or primary T-cells. Percentage of Biotin+/CD19+ CEM or T-cells (a) were plotted against amount of labelled biotin recombinant protein (b).

Figure 9:
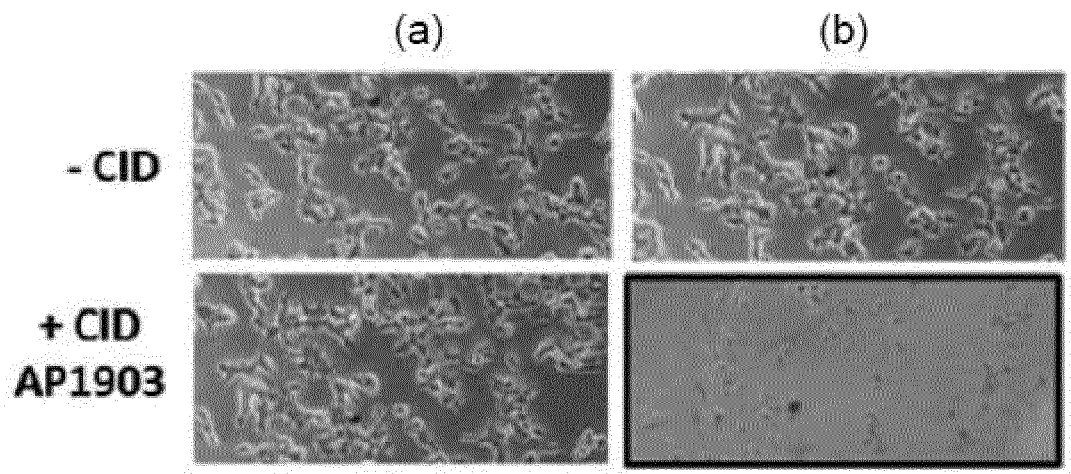

FIG. 9: Safety switch of the iCASP9/AP1903 suicide system cassette after Chemical Inducer Dimerizer (10 nM CID) exposure. (a) 293T cells, (b) IL-1RAP CAR 293T cells.

Figure 10:
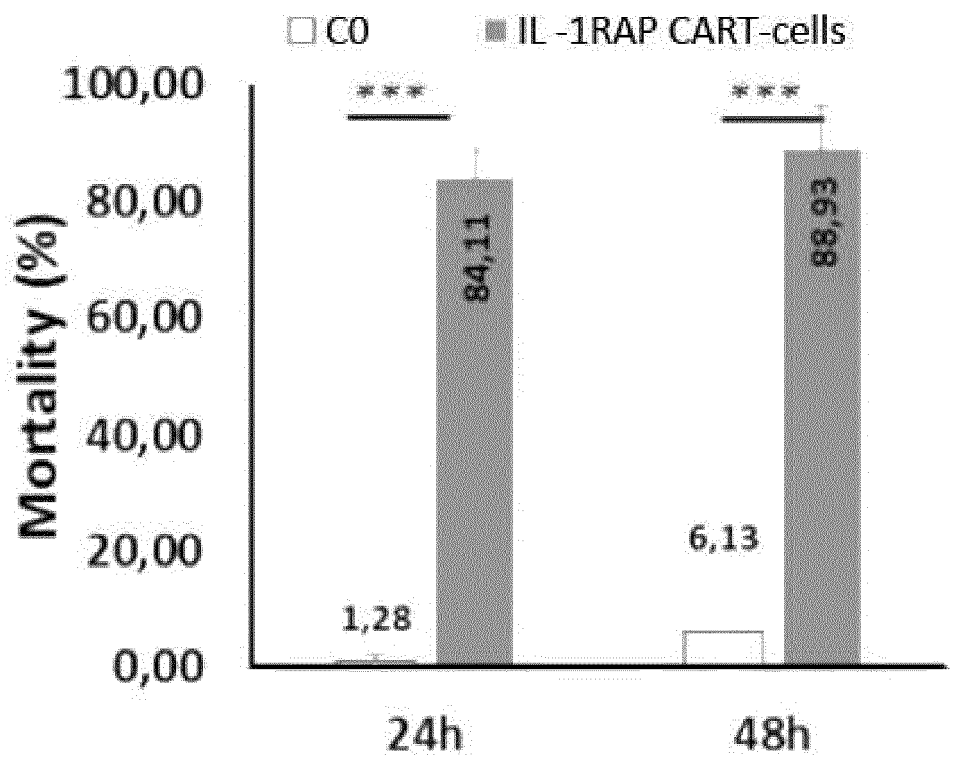

FIG. 10: elimination of IL-1RAP CART cells after 24 h or 48 h CID exposure compared to untransduced T cells (CO) (*** $p<0.001$, n=3).

FIG. 11: Flow cytometry (11A) and western blot (11B) of isoform 1 (v1) and isoform 3 (v5). (a) actin, (b) IL-1RAP-v1 or v5 (72 kDa), (1) total cellular K562 protein, (2) medium supernatant from K562 culture.

Figure 12:
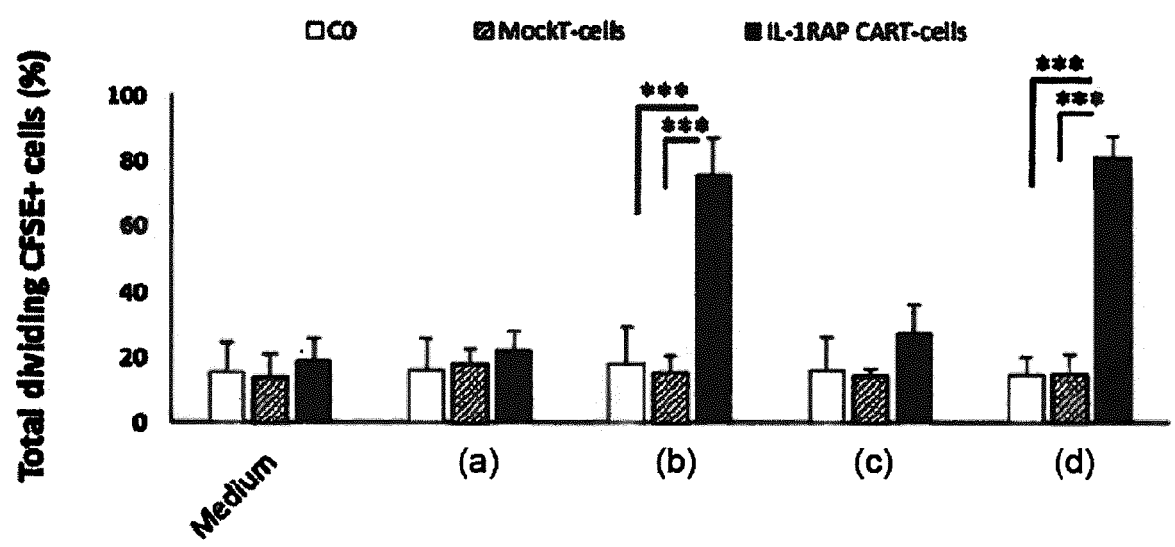

FIG. 12: Proliferative capability of IL-1RAP CART cells triggered by the IL-1RAP target expressing cells by a co-culture of CFSE stained CO, mock or IL-1RAP CART cells in presence of K562 (a), K562-v1 (b), -v5 (c) or KU812 (d) cell lines. ($p<0,001$, n=4)

Figure 13:
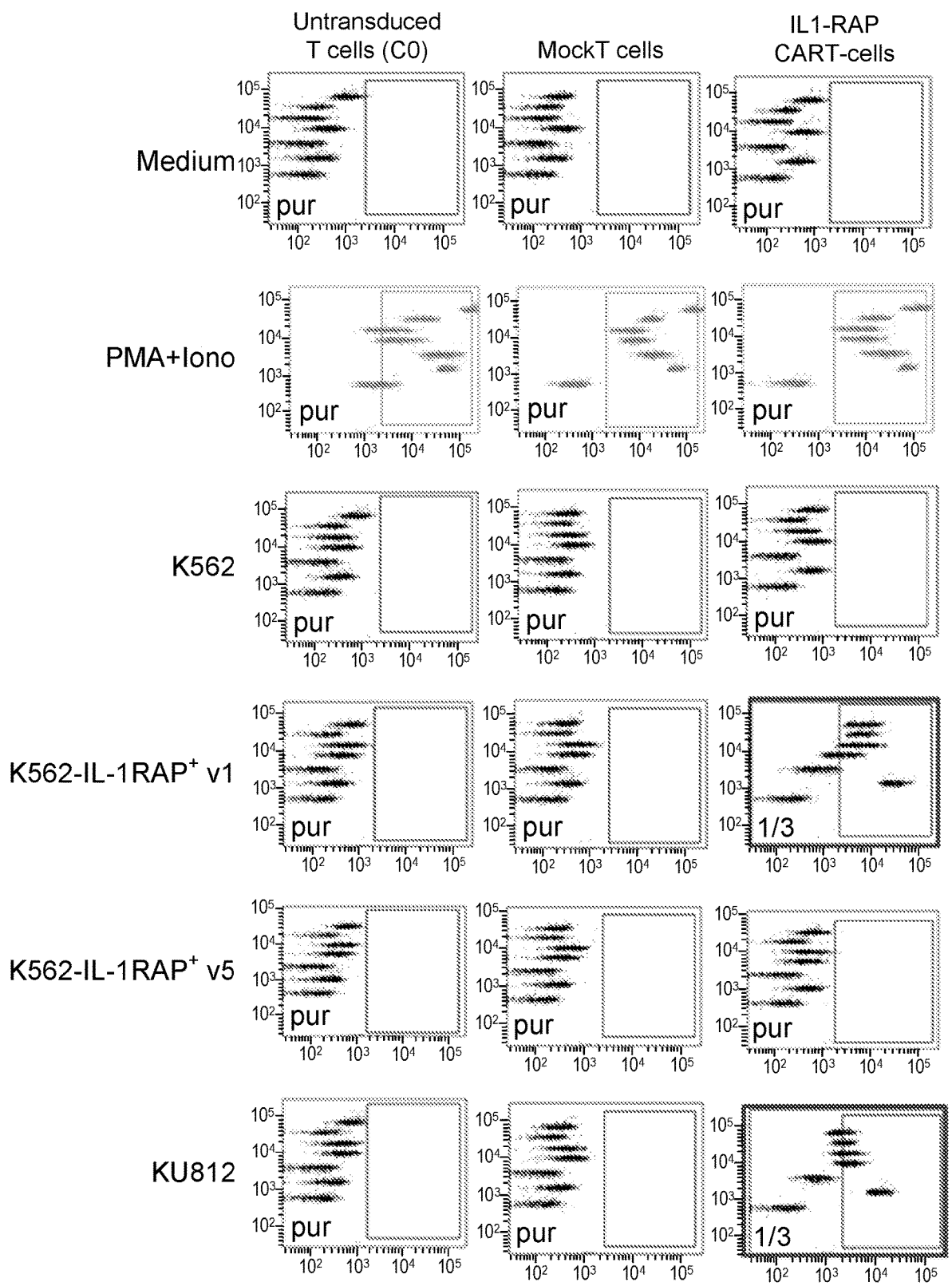

FIG. 13: Measure of Th1/Th2/Th17 cytokines in the supernatant after coculturing with CO (a), Mock T cells (b) or CART cells (c).

Figure 14:
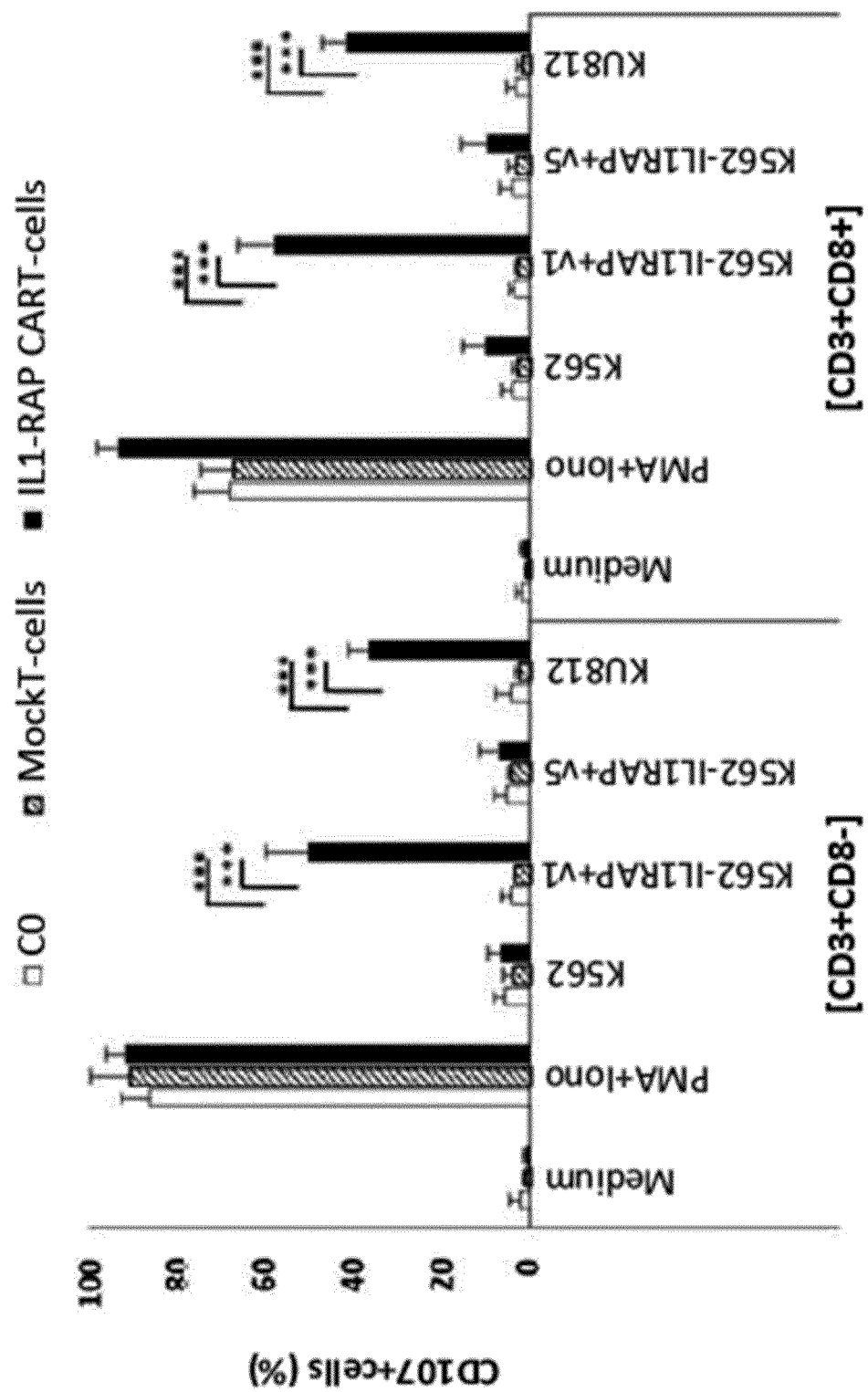

FIG. 14: CD107a&b degranulation assay applied on IL-1RAP CART cells, cocultured, against IL-1RAP+ (K532-V1, KU812) expressing target cells. Effector were treated with monensin and stained with CD107a and CD107b mAbs 1 h at 37° C. After 5 h, CD3+/CD19+/CD8+ cells were analyzed by flow cytometry for CD107a and CD107b staining. PMA/Iono activation was used as control. ($p<0.001$, n=4).

Figure 15:
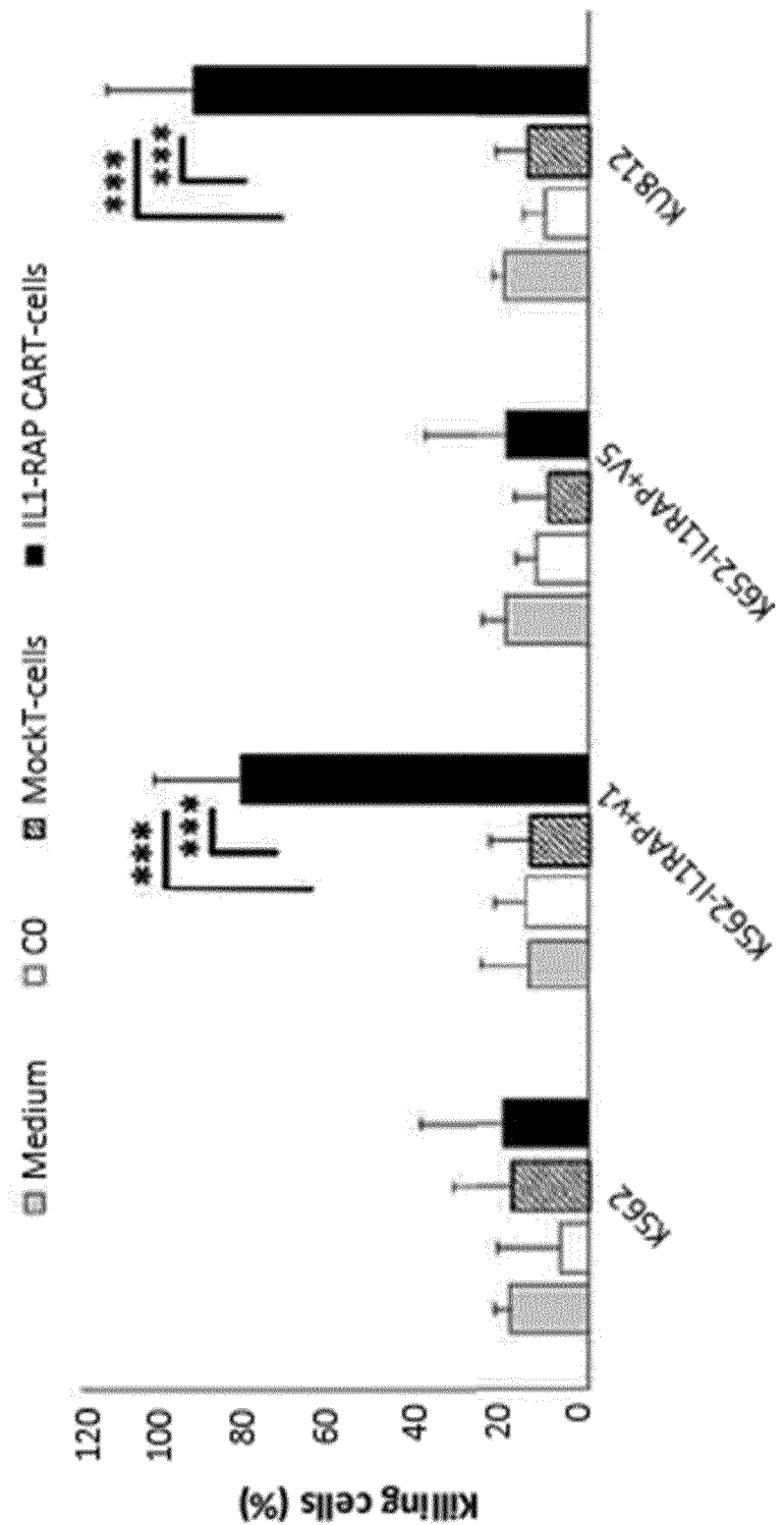

FIG. 15: IL-1RAP dependent cytolytic potency of IL-1RAP CAR expressing T cells in-vitro by fluorescent (eFluor) and 7-AAD staining. Untransduced or mock-transduced T cells were used as control. (p<0.001, n=4).

Figure 16:
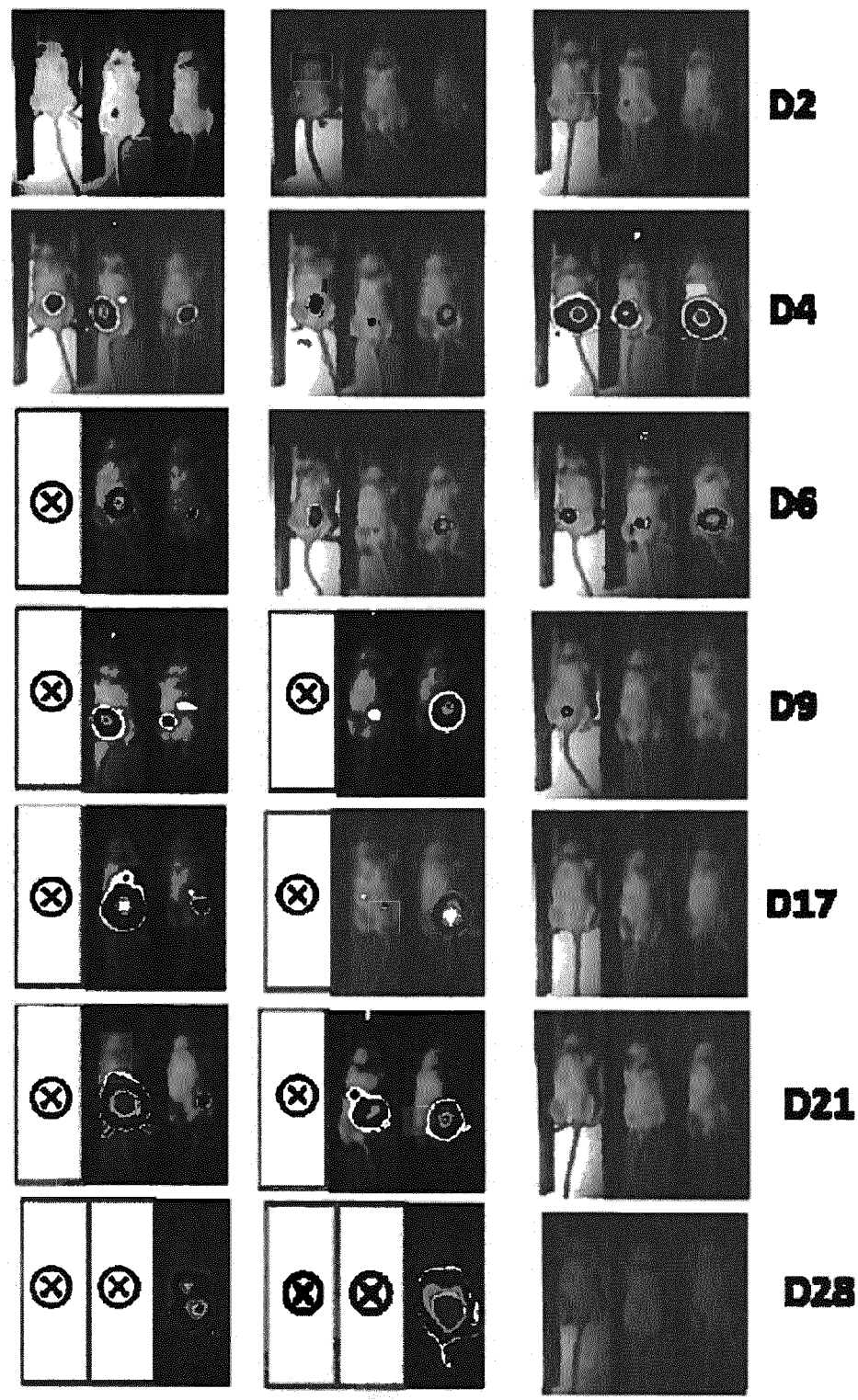

FIG. 16: Murine experiment. A/NSG mice K562 xenograft model. B/BLI analysis of mice of different groups from day 2 to day 28. (0): dead mice. Left panel: untreated, middle: Mock T cells, right panel: IL-1RAP CART cells.

FIG. 17: In vitro toxicity against primary IL-1RAP+ circulating cells from a CML patient. Left, Kinetic quantification of the BCR-ABL1 transcript ratio (% on International Scale) according to the Europe Against Cancer (EAC) method and recommendations. RM3.0, RM4.0, RM4.5, and RM5.0 represent molecular response levels corresponding to a decrease of 3, 4, 4.5, and 5 Log, respectively. IM400: imatinib 400 mg/day, DAS100: dasatinib 100 mg/day, BOS400: bosutinib 400 mg/day, NIL600: nilotinib 600 mg/day. Right, CD3+/CD19+ staining and flow cytometric analysis of the transduction efficiency of PBMCs from a CML patient.

Figure 18:
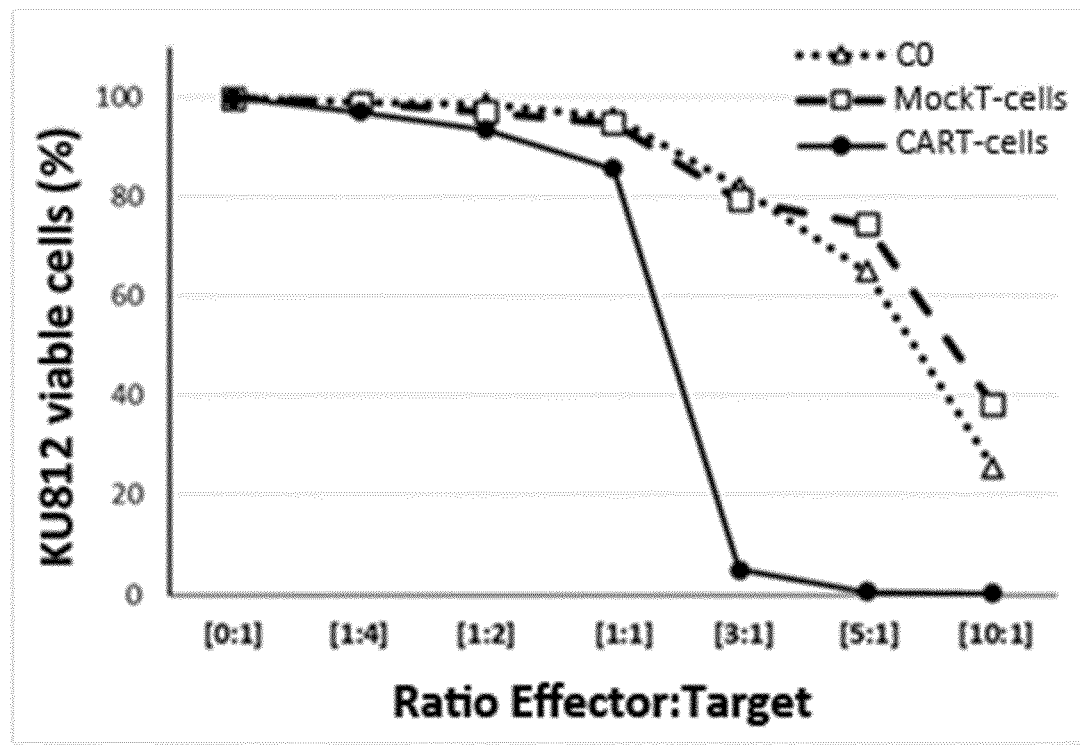

FIG. 18: Graphical representation of persisting viable KU812 cells within the FSC+/7-AAD-gate after coculture of effectors CO, Mock-T, or CAR T cells, labeled with eFluor with KU812 cells at various E:T ratios. Graphical representation of persisting viable KU812 cells within the FSC+/7-AAD-gate.

Figure 19:
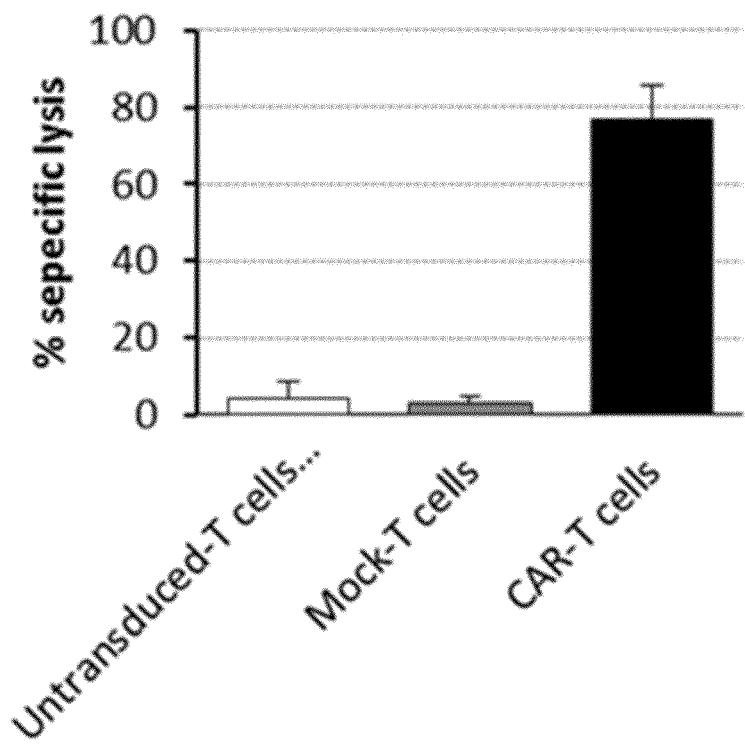

FIG. 19: In vitro toxicity against primary IL-1RAP+ circulating cells from a CML patient. Percentage of total killed target calculated from duplicate experiments. Results are presented as mean±SD.

Figure 20:
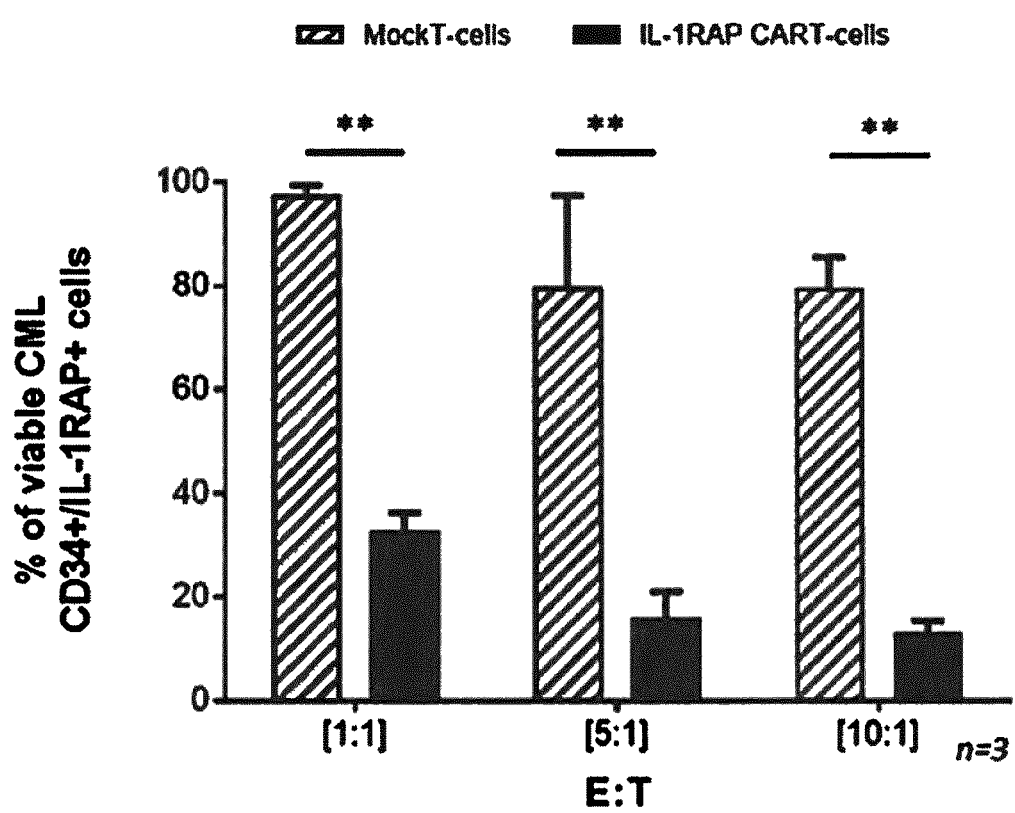

FIG. 20: Cytotoxicity of IL-1RAP CAR or Mock T cells against their respective CML autografts at various effector:target (E:T) ratios. Aggregate results of three independent experiments from three different CML patients. The percentage of remaining viable CD34+/IL-1RAP+ cells calculated from control cells (CO) is provided. **p<0.01.

FIG. 21: Autologous IL-1RAP CART-cells produced from PBMC of CML patients (n=3), still alive and actually under different TKIs treatment for more than 20 years [min: 16y-max: 21y] or free of treatment, were co-cultured in-vitro with their respective cryopreserved autologous Peripheral Blood Stem Cell grafts (PBSC, harvested at time of their diagnosis, more than 20 years back). CML patients, Peripheral Blood Stem Cell autografts characteristics. Ø: Treatment free; IFNγ: Interferony; IM: Imatinib; DAS: Dasatinib; NIL: Nilotinib; PON: Ponatinib; BOS: Bosutinib.

FIG. 22: (A) Tissue microarray. Representative #A3C3 staining of an US Food and Drug Administration standard frozen tissue array, including 90 tissue cores (30 organs) of 3 individual donors per organ (US Biomax, Rockville, MD, USA). Immunostaining was detected using the UltraView Universal DAB Detection Kit (Ventana, USA). Images were acquired and analyzed with NDP.view 2.0 software. Displayed are the tissues that showed some degree of staining with #A3C3 mAb in at least one individual out of three analyzed. (Scale bars, 100 μm.) High IL-1RAP (KU812)— or negative (Raji)-expressing cell lines were respectively used as positive or negative controls. (B) IL-1RAP R&D (red) or #A3C3 (blue) staining of HMEC-1 dermal endothelial cell line. Isotype IgG1 (gray) is depicted as overlay. RFI is provided for both staining.

FIG. 23: Effect of IL-1RAP CAR T cells on healthy hematopoietic cells and efficiency of the safety suicide gene iCASP9 cassette. (A) IL-1RAP cell surface expression on peripheral blood (left) or bone marrow (right) cells from healthy donors (n=5). SSC-A/CD45+ allowed discrimination of subpopulations as lymphocytes (SSC-A low), monocytes (CD33+), granulocytes (SSC-A high), or HSCs (CD33−/CD34+). RFI was calculated from isotype staining and provided in each window. (B) Representative (1 of 3) IL-1RAP staining of whole human cord blood cells. IL-1RAP staining is provided for whole CD34+, CD34+/CD38−, and CD34+/CD38+ HSC cord blood subpopulations. (C) IL-1RAP-positive cells among CD34+ cells in cord blood (CB, n=5) or bone marrow (BM) from healthy donors (n=5) compared to CD34+ cells from the BM (n=10) or peripheral blood (PB, n=10) from CML patients. (D) Left, Dot plot of SSC-A/CD45+ granulocyte (G), monocyte (M), and lymphocyte (L) subpopulations cultured in the presence of different effector:target (E:T) ratios of autologous non-transduced T cells or Mock or IL-1RAP CAR T cells. Right, Relative percentage of alive cells among lymphocytes (square), monocytes (circle), and granulocytes (triangle), normalized to nontransduced autologous T cells (CO) co-cultured 24 h with autologous Mock T cells (dashed line) or IL-1RAP CAR T cells (solid line). (E) Relative percentage of alive cells among the monocyte (square), KU812 (circle), or K562 (triangle) subpopulations in the presence of different E:T ratios of Mock (black, dashed line) or IL-1RAP CAR T cells (white, solid line). Percentages were calculated using absolute cell number determined using Trucount™ tubes based on 5000 fluorescent-bead cytometry acquisition. (F) Left, Gating strategy and analysis for absolute count of CID AP1903-induced cell death. Nontransduced (CO) or IL-1RAP CAR T cells were exposed to medium alone or medium +CID (20 nM, 24 h). The quantification was performed after acquiring 5000 fluorescent beads. Killing efficiency was normalized to control cells (untreated cells). Cell killing was calculated as follows: % Dead cells=[1−(absolute number of viable cells in AP1903-treated cells/absolute number of viable cells in untreated cells)]×100. (D) Absolute percentage of mortality. 24 h or 48 h CO or IL-1RAP CAR (gated on CD3+/CD19+) T cell CID exposure. Right, Results are means from three independent experiments.  p<0.001. (G) Absolute quantification of IL-1RAP CAR T cells injected in a tumor (CML KU812, i.v.) xenograft NSG model 24 h after i.p. AP1903 (white bars) treatment (n=3 mice/group). Mice infused with control T cells (CO) were used as controls (n=2 mice/group). p<0.01. Number of cells is provided per ml of peripheral blood.

Figure 24:
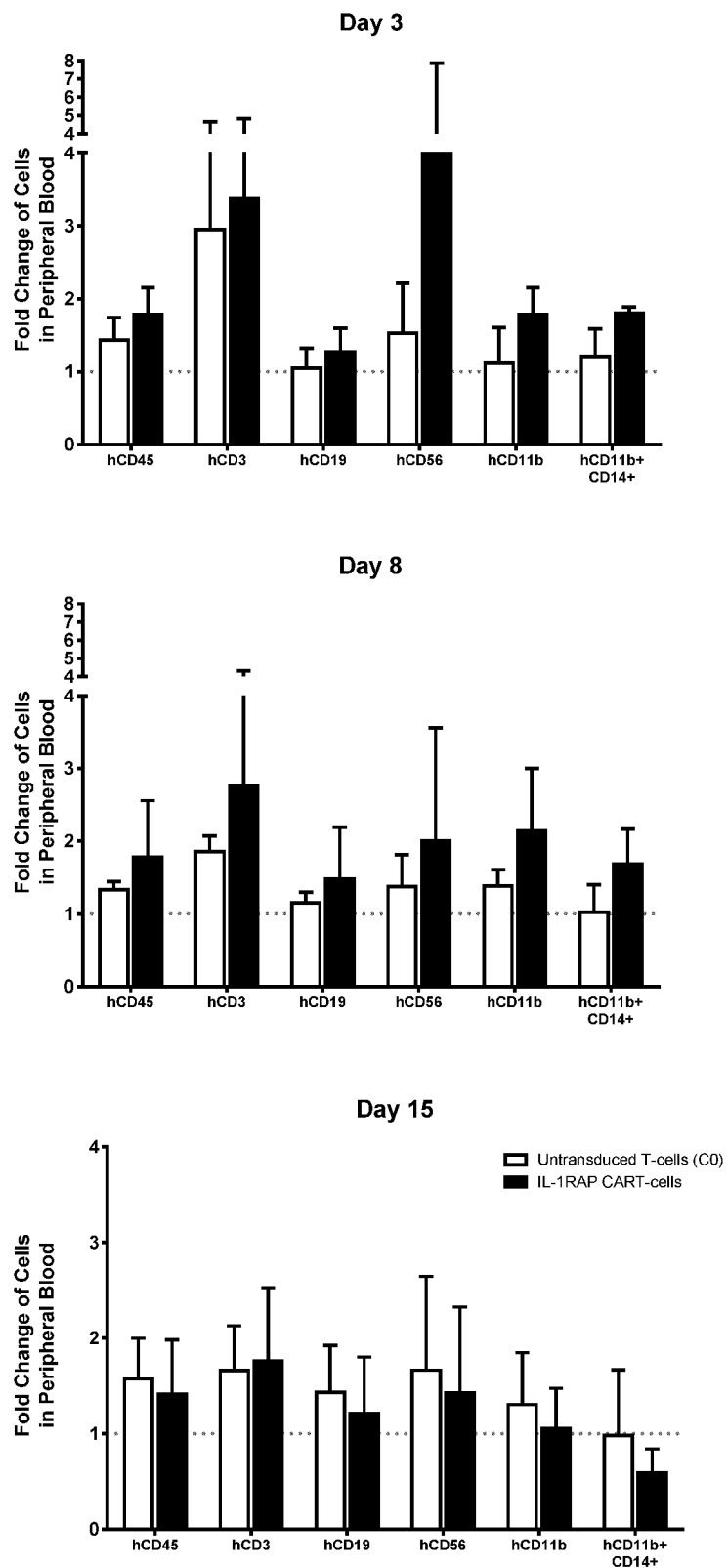

FIG. 24: Experimental immunosafety human CD34+ engrafted NOG murine model in order to investigate specific toxicities of autologous IL-1RAP CART-cells against HSC and/or immune cells on a human-CD34+ cord blood cell engrafted/NOG murine model (hu-NOG). Briefly, 10.10E6 autologous CART-cells or control T-cells (CO) (produced from human CD45+ cell-sorted from murine PBMC, Spleen or Bone Marrow) were infused. Monitoring of mature immune cells (hCD3+, hCD19+, hCD56+, hCD14+, hCD11b+) was assessed at various times post infusion (Day 5, 8 and 15) by cytometry. Fold changes were calculated from immunophenotyping reference acquired at day −7 prior to CART-cells infusion. compare to time of peripheral blood harvesting (Day −9). Fold change of different immunocompetent cell subpopulations at days 3, 8 and 15 after untransduced (CO, white bars) or IL-1RAP CART-cells (black bars) infusion compared to time of peripheral blood harvesting (Day −9). Cells count was performed from peripheral blood harvested by retro-orbital samples and Fold Change was calculated against day −7 reference. n.s: not significant.

Figure 25:
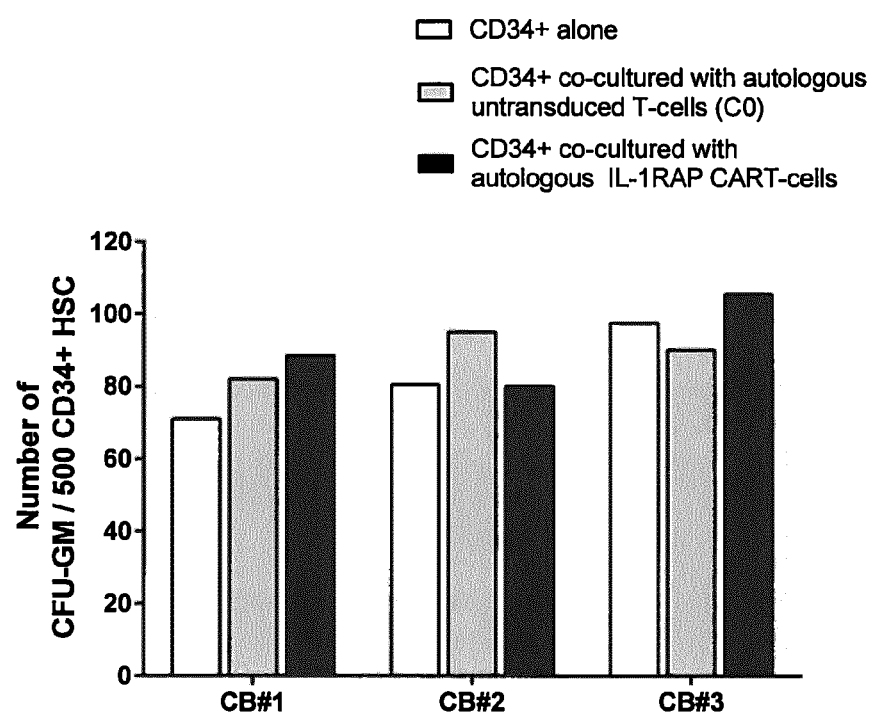

FIG. 25: Colony Forming Unit (CFU-GM) experiment {Giavridis, 2018 #1861} from CD34+ HSC harvested from 3 different Cord Blood and cultured alone (white bars) or co-cultured with their respective autologous untransduced (CO, gray bars) or IL-1RAP CART-cells (black bars).

Figure 26:
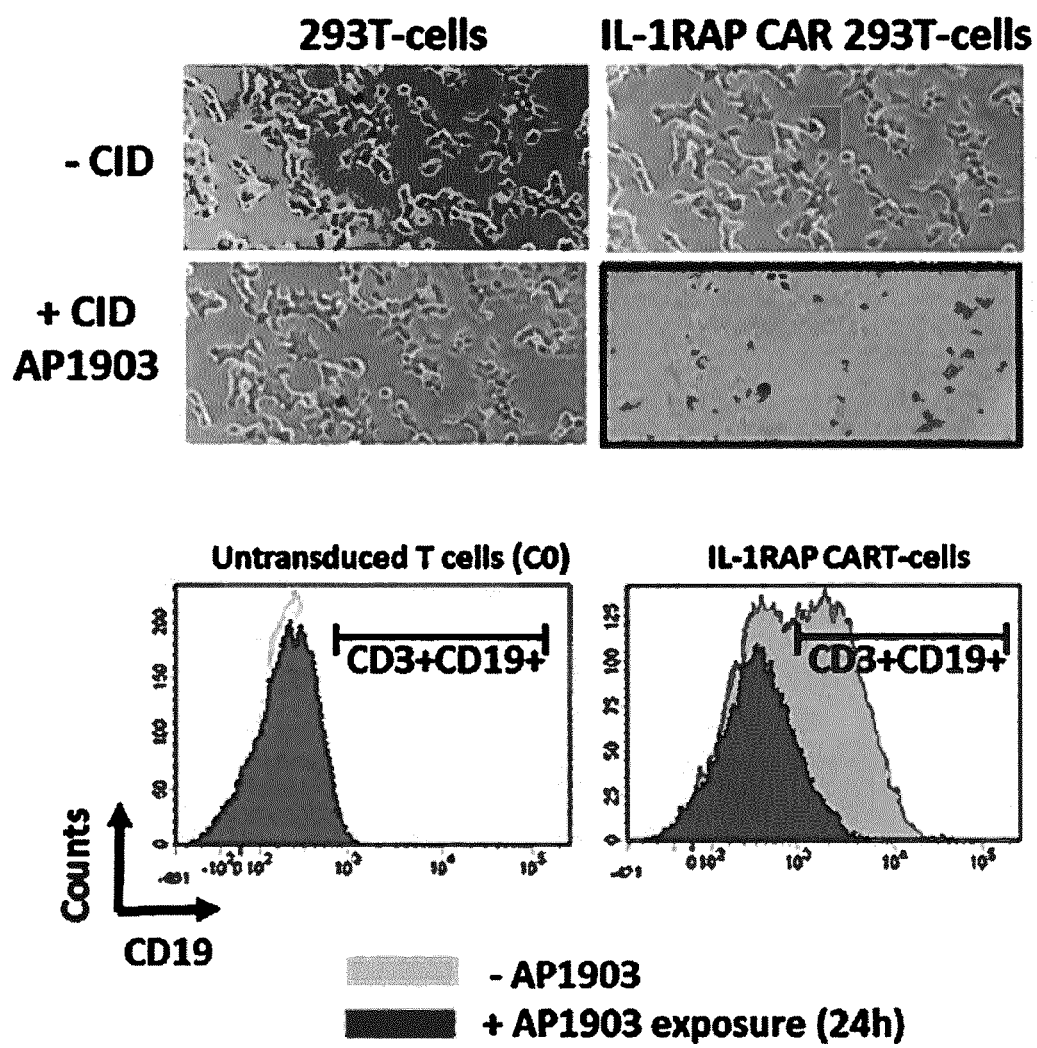

FIG. 26: Upper panel: Evaluation by optical microscopy of the CID effect on transduced 293T cells. Lower panel: Flow cytometry analysis of IL-1RAP CART cells after CID AP1903 exposure. Flow cytometry analysis after CID exposure (20 nM, 24 h, dark gray) or not (light gray) on untransduced T cells (CO) and on GMTC mixture, expressing or not IL-1RAP CAR. CD3+/CD19+ staining allowed discrimination of GMTCs expressing CAR.

The following Table summarizes the sequence identifiers.

TABLE 1 sequence listing

| SEQ ID | Name | Sequence |
|---|---|---|
| SEQ ID NO: 1 | Nucleotide sequence coding chain H (VH) of murine scFv anti-IL-1RAP (with leader sequence in bold) | atgggatggagctgtatcatcctcttcttggt agcaacagctacaggtgtcaactcccaggtc caactgcagcagcctggggctgagcttatgatgcct ggggcttcagtgaaagtgtcctgcgaggcttctggc tacacattcactgactcctggatgcactgggtgaag cagaggcctggacaaggccttgagtggatcggag cgattgatccttctgatagttatactacctataatcaa aaattcacgggcaaggccacattgagtgtagacga atcctccaacacagcctacatgcagctcagcagcct gacatctgaggactctgcggtctattactgtgcaag gtattactccggtagtaactacatatcgccctttcctt actggggccaagggactctggtcactgtctctgca |
| SEQ ID NO: 2 | Amino acid sequence of chain H (VH) of murine scFv anti-IL-1RAP (with leader sequence in bold) | MGWSCIILFLVATATGVNSQVQLQQPG AELMMPGASVKVSCEASGYTFTDSWMHW VKQRPGQGLEWIGAIDPSDSYTTYNQKFT GKATLSVDESSNTAYMQLSSLTSEDSAVY YCARYYSGSNYISPFPYWGQGTLVTVSA |
| SEQ ID NO: 3 | Nucleotide sequence coding chain K (VL) of murine scFv anti-IL-1RAP | atggagtcacagattcaggtctttgtattcgtgtttct ctggttgtctggtgttgacggagacattgtgatgac ccagtctcacaaattcatgtccacatcagtaggaga cagggtcaccatcacctgcaaggccagtctggatg tgagtactgctgtggcctggtatcaacagaaacca ggacaatctcctaaactactgatttactcggcatcct accggtacactggagtccctgatcgcttcactggca gtggatctgggacggatttcactttcaccatcagca gtgtgcaggctgaagacctggcagtttattactgtc agcaacattatagtcctccattcacgttcggctcgg ggacaaacttggagataaaac |
| SEQ ID NO: 4 | Amino acid sequence of chain K (VL) of murine scFv anti-IL-1RAP | MESQIQVFVFVFLWLSGVDGDIVMTQSHK FMSTSVGDRVTITCKASLDVSTAVAWYQQ KPGQSPKLLIYSASYRYTGVPDRFTGSGSG TDFTFTISSVQAEDLAVYYCQQHYSPPFTF GSGTNLEIK |
| SEQ ID NO: 5 | Linker between the VH and VL domains (aa) | GGSGGGGSGGGGSVD |
| SEQ ID NO: 6 | CDR1 of the light chain (aa) | LDVSTA |
| SEQ ID NO: 7 | CDR2 of the light chain (aa) | SAS |
| SEQ ID NO: 8 | CDR3 of the light chain (aa) | QQHYSPPFT |
| SEQ ID NO: 9 | CDR1 of the light chain (nucleotides) | ctggatgtgagtactgct |
| SEQ ID NO: 10 | CDR2 of the light chain (nucleotides) | tcggcatcc |
| SEQ ID NO: 11 | CDR3 of the light chain (nucleotides) | cagcaacattatagtcctccattcacg |
| SEQ ID NO: 12 | CDR1 of the heavy chain (aa) | GYTFTDSW |
| SEQ ID NO: 13 | CDR2 of the heavy chain (aa) | IDPSDSYT |
| SEQ ID NO: 14 | CDR3 of the heavy chain (aa) | ARYYSGSNYISPFPY |
| SEQ ID NO: 15 | CDR1 of the heavy chain (nucleotides) | ggctacacattcactgactcctgg |
| SEQ ID NO: 16 | CDR2 of the heavy chain (nucleotides) | attgatccttctgatagttatact |

TABLE 1 -continued sequence listing

| SEQ ID | Name | Sequence |
|---|---|---|
| SEQ ID NO: 17 | CDR3 of the heavy chain (nucleotides) | gcaaggtattactccggtagtaactacatatcgccct ttccttac |
| SEQ ID NO: 18 | Amino acid sequence of murine scFv anti-IL-1 RAP (i.e. from #A3C3 CAR) | MGWSCIILFLVATATGVNSQVQLQQPG AELMMPGASVKVSCEASGYTFTDSWMHW VKQRPGQGLEWIGAIDPSDSYTTYNQKFT GKATLSVDESSNTAYMQLSSLTSEDSAVY YCARYYSGSNYISPFPYWGQGTLVTVSA GGSGGGSGGGGSVDMESQIQVFVFVFL WLSGVDGDIVMTQSHKFMSTSVGDRVTI TCKASLDVSTAVAWYQQKPGQSPKLLIYS ASYRYTGVPDRFTGSGSGTDFTFTISSVQ AEDLAVYYCQQHYSPPFTFGSGTNLEIK |

The sequences of the hinge region of IgG1, IgG4, CD8alpha, 4-1BB, CD3 zeta, CD28 and ICasp9 genes can be found on Genbank.

The practice of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., Molecular Cloning: A Laboratory Manual (3rd Edition, 2001); Sambrook, et al., Molecular Cloning: A Laboratory Manual (2nd Edition, 1989); Maniatis et al., Molecular Cloning: A Laboratory Manual (1982); Ausubel et al., Current Protocols in Molecular Biology (John Wiley and Sons, updated July 2008); Short Protocols in Molecular Biology: A Compendium of Methods from Current Protocols in Molecular Biology, Greene Pub. Associates and Wiley-Interscience; Glover, DNA Cloning: A Practical Approach, vol. I & II (IRL Press, Oxford, 1985); Anand, Techniques for the Analysis of Complex Genomes, (Academic Press, New York, 1992); Transcription and Translation (B. Hames & S. Higgins, Eds., 1984); Perbal, A Practical Guide to Molecular Cloning (1984); Harlow and Lane, Antibodies, (Cold Spring Harbor Laboratory Press, Cold Spring Harbor, N.Y., 1998); Current Protocols in Immunology, Q. E. Coligan, A. M. Kruisbeek, D. H. Margulies, E. M. Shevach and W. Strober, eds., 1991); Annual Review of Immunology; as well as monographs in journals such as Advances in Immunology.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein.

As would be understood by the skilled person and as described elsewhere herein, a complete antibody comprises two heavy chains and two light chains. Each heavy chain consists of a variable region and a first, second, and third constant regions, while each light chain consists of a variable region and a constant region. Mammalian heavy chains are classified as α, δ, ε, γ, and μ, and mammalian light chains are classified as λ or κ. Immunoglobulins comprising the α, δ, ε, γ, and μ heavy chains are classified as immunoglobulin (Ig)A, IgD, IgE, IgG, and IgM. The complete antibody forms a "Y" shape. The stem of the Y consists of the second and third constant regions (and for IgE and IgM, the fourth constant region) of two heavy chains bound together and disulfide bonds (inter-chain) are formed in the hinge. Heavy chains γ, α and δ have a constant region composed of three tandem (in a line) Ig domains, and a hinge region for added flexibility; heavy chains μ and ε have a constant region composed of four immunoglobulin domains. The second and third constant regions are referred to as "CH2 domain" and "CH3 domain", respectively. Each arm of the Y includes the variable region and first constant region of a single heavy chain bound to the variable and constant regions of a single light chain. The variable regions of the light and heavy chains are responsible for antigen binding.

Light and heavy chain variable regions contain a "framework" region interrupted by three hypervariable regions, also called "complementarity-determining regions" or "CDRs." The CDRs can be defined or identified by conventional methods, such as by sequence according to Kabat et al (Wu, TT and Kabat, E. A., J Exp Med. 132(2):211-50, (1970); Borden, P. and Kabat E. A., PNAS, 84: 2440-2443 (1987); (see, Kabat et al., Sequences of Proteins of Immunological Interest, U.S. Department of Health and Human Services, 1991), or by structure according to Chothia et al (Choithia, C. and Lesk, A. M., J Mol. Biol., 196(4): 901-917 (1987), Choithia, C. et al, Nature, 342: 877-883 (1989)).

The sequences of the framework regions of different light or heavy chains are relatively conserved within a species, such as humans. The framework region of an antibody, that is the combined framework region of the constituent light and heavy chains, serves to position and align the CDRs in three-dimensional space. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, the CDRs located in the variable domain of the heavy chain of the antibody are referred to as CDRH1, CDRH2, and CDRH3, whereas the CDRs located in the variable domain of the light chain of the antibody are referred to as CDRL1, CDRL2, and CDRL3. Antibodies with different specificities (i.e., different combining sites for different antigens) have different CDRs.

References to "VH" or "$V_H$" refer to the variable region of an immunoglobulin heavy chain, including that of an antibody, Fv, scFv, Fab, or other antibody fragment as disclosed herein.

References to "VL" or "$V_L$" refer to the variable region of an immunoglobulin light chain, including that of an antibody, Fv, scFv, dsFv, Fab, or other antibody fragment as disclosed herein.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

The articles "a," "an," and "the" are used herein to refer to one or to more than one (i.e., to at least one) of the grammatical object of the article.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

Throughout this specification, unless the context requires otherwise, the words "comprise", "comprises" and "comprising" will be understood to imply the inclusion of a stated step or element or group of steps or elements but not the exclusion of any other step or element or group of steps or elements.

Reference throughout this specification to "one embodiment", "an embodiment", "a particular embodiment", "a certain embodiment", "an additional embodiment" or "a further embodiment" or combinations thereof means that a particular feature, structure or characteristic described in connection with the embodiment is included in at least one embodiment of the present invention.

For the purposes of the present invention, the "identity" or "homology" is calculated by comparing two aligned sequences in a comparison window. The alignment of the sequences makes it possible to determine the number of positions (nucleotides or amino acids) common to the two sequences in the comparison window. The number of common positions is then divided by the total number of positions in the comparison window and multiplied by 100 to obtain the percentage of homology. The determination of the percentage of sequence identity can be done manually or by using well-known computer programs.

The present invention provides immune effector cells genetically engineered with vectors designed to express chimeric antigen receptors that redirect cytotoxicity toward tumor cells. These genetically engineered receptors referred to herein as chimeric antigen receptors (CARs). CARs are molecules that combine antibody-based specificity for a target antigen (e.g. tumor antigen) with a T cell receptor-activating intracellular domain to generate a chimeric protein that exhibits a specific anti-tumor cellular immune activity. As used herein, the term, "chimeric," describes being composed of parts of different proteins or DNAs from different origins.

The invention refers to an isolated nucleic acid molecule encoding a chimeric antigen receptor (CAR), wherein the CAR comprises an antibody or antibody fragment which includes a anti-IL-1RAP binding domain, a transmembrane domain, and an intracellular signaling domain comprising at least a stimulatory domain, and wherein said anti-IL-1RAP binding domain comprises:

(i) a light chain comprising a complementary determining region 1 (CDR1) having at least 80%, 85%, 90%, 95%, 96%, 97%, 98%, 99% or having 100% identity with the amino acid sequence SEQ ID NO: 6, a complementary determining region 2 (CDR2) having at least 80%, 85%, 90%, 95%, 96%, 97%, 98%, 99% or having 100% identity with the amino acid sequence SEQ ID NO: 7 and a complementary determining region 3 (CDR3) having at least 80%, 85%, 90%, 95%, 96%, 97%, 98%, 99% or having 100% identity with the amino acid sequence SEQ ID NO: 8, and (ii) a heavy chain comprising a complementary determining region 1 (CDR1) having at least 80%, 85%, 90%, 95%, 96%, 97%, 98%, 99% or having 100% identity with the amino acid sequence SEQ ID NO: 12, a complementary determining region 2 (CDR2) having at least 80%, 85%, 90%, 95%, 96%, 97%, 98%, 99% or having 100% identity with the amino acid sequence SEQ ID NO: 13 and a complementary determining region 3 (CDR3) having at least 80%, 85%, 90%, 95%, 96%, 97%, 98%, 99% or having 100% identity with the amino acid sequence SEQ ID NO: 14.

The main characteristic of CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific co-receptors.

As used herein, the terms, "binding domain," "extracellular binding domain," "antigen-specific binding domain," and "extracellular antigen specific binding domain," are used interchangeably and provide a CAR with the ability to specifically bind to the target antigen of interest. A binding domain may comprise any protein, polypeptide, oligopeptide, or peptide that possesses the ability to specifically recognize and bind to a biological molecule {e.g., a cell surface receptor or tumor protein, lipid, polysaccharide, or other cell surface target molecule, or component thereof). A binding domain includes any naturally occurring, synthetic, semi-synthetic, or recombinantly produced binding partner for a biological molecule of interest. The terms "specific binding affinity" or "specifically binds" or "specifically bound" or "specific binding" or "specifically targets" as used herein, describe binding of one molecule to another at greater binding affinity than background binding. A binding domain (or a CAR comprising a binding domain or a fusion protein containing a binding domain) "specifically binds" to a target molecule if it binds to or associates with a target molecule with an affinity or Ka (i.e., an equilibrium association constant of a particular binding interaction with units of 1/M) of, for example, greater than or equal to about $10^5 M^{-1}$. Affinities of binding domain polypeptides and CAR proteins according to the present disclosure can be readily determined using conventional techniques like competitive ELISA (enzyme-linked immunosorbent assay).

The antibody is a human antibody, a murine antibody, or a humanized antibody.

In certain preferred embodiments, the antibody is a humanized antibody (such as a humanized monoclonal antibody) that specifically binds to a surface protein on a tumor cell. A "humanized" antibody is an immunoglobulin including a human framework region and one or more CDRs from a non-human (for example a mouse, rat, or synthetic) immunoglobulin. Hence, all parts of a humanized immunoglobulin, except possibly the CDRs, are substantially identical to corresponding parts of natural human immunoglobulin sequences. Humanized or other monoclonal antibodies can have additional conservative amino acid substitutions, which have substantially no effect on antigen binding or other immunoglobulin functions. Humanized antibodies can be constructed by means of genetic engineering (see for example, U.S. Pat. No. 5,585,089).

Antibodies include antigen binding fragments thereof, such as Fab fragments, Fab' fragments, F(ab)'2 fragments, F(ab)'3 fragments, Fv, single chain Fv proteins ("scFv") and portions of full length antibodies responsible for antigen binding. The term also includes genetically engineered forms such as chimeric antibodies (for example, humanized murine antibodies), heteroconjugate antibodies (such as, bispecific antibodies) and antigen binding fragments thereof.

"Single-chain Fv" or "scFv" antibody fragments comprise the VH and VL domains of antibody, wherein these domains are present in a single polypeptide chain and in either orientation (e.g., VL-VH or VH-VL). Single chain antibodies may be cloned from the V region genes of a hybridoma specific for a desired target. The production of such hybridomas has become routine. A technique which can be used for cloning the variable region heavy chain (VH) and variable region light chain (VL) has been described, for example, in Orlandi et at, PNAS, 1989; 86: 3833-3837.

Generally, the scFv polypeptide further comprises a polypeptide linker between the VH and VL domains which enables the scFv to form the desired structure for antigen binding.

CARs contemplated herein, may comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

Illustrative examples of linkers include glycine polymers (G)n; glycine-serine polymers (Gi_sSi_5)n, where n is an integer of at least one, two, three, four, or five; glycine-alanine polymers; alanine-serine polymers; and other flexible linkers known in the art. Glycine and glycine-serine polymers are relatively unstructured, and therefore may be able to serve as a neutral tether between domains of fusion proteins such as the CARs described herein. Glycine accesses significantly more phi-psi space than even alanine, and is much less restricted than residues with longer side chains {see Scheraga, Rev. Computational Chem. 1 1173-142 (1992)). The ordinarily skilled artisan will recognize that design of a CAR in particular embodiments can include linkers that are all or partially flexible, such that the linker can include a flexible linker as well as one or more portions that confer less flexible structure to provide for a desired CAR structure.

In a particular embodiment, the linker is between the VH and VL domains.

In a particular embodiment, the linker comprises or consists in the amino acid sequence of SEQ ID NO° 5.

In one embodiment, the IL-1RAP binding domain is a scFv comprising a light chain variable region comprising an amino acid sequence having at least one, two or three modifications but not more than 30, 20 or 10 modifications of an amino acid sequence of a light chain variable regions of SEQ ID NO: 4 and a heavy chain variable region comprising an amino acid sequence having at least one, two or three modifications but not more than 30, 20 or 10 modifications of an amino acid sequence of a heavy chain variable region of SEQ ID NO: 2.

Preferably, the IL-1RAP binding domain is a scFv comprising (i) a light chain variable region comprising a complementary determining region 1 (CDR1) having at least 80%, 85%, 90%, 95%, 96%, 97%, 98%, 99% or having 100% identity with the amino acid sequence SEQ ID NO: 6, a complementary determining region 2 (CDR2) having at least 80%, 85%, 90%, 95%, 96%, 97%, 98%, 99% or having 100% identity with the amino acid sequence SEQ ID NO: 7 and a complementary determining region 3 (CDR3) having at least 80%, 85%, 90%, 95%, 96%, 97%, 98%, 99% or having 100% identity with the amino acid sequence SEQ ID NO: 8, and (ii) a heavy chain variable region comprising a complementary determining region 1 (CDR1) having at least 80%, 85%, 90%, 95%, 96%, 97%, 98%, 99% or having 100% identity with the amino acid sequence SEQ ID NO: 12, a complementary determining region 2 (CDR2) having at least 80%, 85%, 90%, 95%, 96%, 97%, 98%, 99% or having 100% identity with the amino acid sequence SEQ ID NO: 13 and a complementary determining region 3 (CDR3) having at least 80%, 85%, 90%, 95%, 96%, 97%, 98%, 99% or having 100% identity with the amino acid sequence SEQ ID NO: 14.

The binding domain of the CAR is generally followed by one or more "hinge regions", which play a role in positioning the antigen binding domain away from the effector cell surface to enable proper cell/cell contact, antigen binding and activation. A CAR generally comprises one or more hinge regions between the binding domain and the transmembrane domain. The hinge region may be derived either from a natural, synthetic, semi-synthetic, or recombinant source.

Preferably, the anti-IL-1RAP binding domain is connected to the transmembrane domain by a hinge region.

In an embodiment, the hinge region comprises the hinge sequence of IgG1 or a sequence with 95-99% identity thereof.

In further embodiments, the hinge region comprises the hinge sequence of IgG4 or a sequence with 95-99% identity thereof. In further embodiments, the hinge region may also comprise the CH2-CH3 region of IgG1 or IgG4 or a sequence with 95-99% identity thereof.

In further embodiments, the hinge region comprises CD8alpha or a sequence with 95-99% identity thereof.

The "transmembrane domain" is the portion of the CAR that fuses the extracellular binding portion and intracellular signaling domain and anchors the CAR to the plasma membrane of the immune effector cell. The transmembrane domain may be derived either from a natural, synthetic, semi-synthetic, or recombinant source.

Preferably, the encoded CAR includes a transmembrane domain of a protein selected from the group consisting of the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD 137 and CD 154, more preferably CD28.

In particular embodiments, CARs contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term "intracellular signaling domain" is meant to include any truncated portion of the intracellular signaling domain sufficient to transducing effector function signal.

It is known that signals generated through the TCR alone are insufficient for full activation of the T cell and that a secondary or co-stimulatory signal is also required. Thus, T cell activation can be said to be mediated by two distinct classes of intracellular signaling domains: primary signaling domains that initiate antigen-dependent primary activation through the TCR (e.g. a TCR/CD3 complex) and co-stimulatory signaling domains that act in an antigen-independent manner to provide a secondary or co-stimulatory signal. In preferred embodiments, a CAR contemplated herein comprises an intracellular signaling domain that comprises one or more "co-stimulatory signaling domain".

In an embodiment, the isolated nucleic acid molecule may encode an intracellular signaling domain comprising at least one costimulatory domain. In this embodiment, the intracellular signaling domain therefore comprises at least one costimulatory domain.

As used herein, the term "co-stimulatory signaling domain," or "co-stimulatory domain", refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen.

Preferably, the at least one costimulatory domain of the functional intracellular signaling domain is obtained from one or more protein selected from the group consisting of OX40, CD2, CD27, CD28, CDS, CD3 zeta, ICAM-1, LFA-1 (CD11a/CD18), ICOS (CD278), and 4-1BB (CD137).

More preferably, the costimulatory domain obtained from 4-1BB (CD137) has a sequence having 95-99% identity with the amino acid sequence of the costimulatory domain of 4-1BB.

More preferably, the costimulatory domain obtained from CD3 zeta has a sequence having 95-99% identity with the amino acid sequence of the costimulatory domain of CD3 zeta.

In another embodiment, the intracellular signaling domain comprises a costimulatory domain obtained from 4-1BB and/or a costimulatory domain obtained from CD3 zeta.

In particular preferred embodiments, a CAR comprises a CD3 primary signaling domain and one or more co-stimulatory signaling domains. The intracellular primary signaling and co-stimulatory signaling domains may be linked in any order in tandem to the carboxyl terminus of the transmembrane domain.

An isolated polypeptide molecule encoded by the nucleic acid molecule of the invention is also contemplated as well as an isolated CAR molecule comprising an antibody or antibody fragment which includes an anti-IL-1RAP binding domain, a transmembrane domain, and an intracellular signaling domain, wherein said anti-IL-1RAP binding domain comprises:

(i) a light chain comprising a complementary determining region 1 (CDR1) having at least 80%, 85%, 90%, 95%, 96%, 97%, 98%, 99% or having 100% identity with the amino acid sequence SEQ ID NO: 6, a complementary determining region 2 (CDR2) having at least 80%, 85%, 90%, 95%, 96%, 97%, 98%, 99% or having 100% identity with the amino acid sequence SEQ ID NO: 7 and a complementary determining region 3 (CDR3) having at least 80%, 85%, 90%, 95%, 96%, 97%, 98%, 99% or having 100% identity with the amino acid sequence SEQ ID NO: 8, and (ii) a heavy chain comprising a complementary determining region 1 (CDR1) having at least 80%, 85%, 90%, 95%, 96%, 97%, 98%, 99% or having 100% identity with the amino acid sequence SEQ ID NO: 12, a complementary determining region 2 (CDR2) having at least 80%, 85%, 90%, 95%, 96%, 97%, 98%, 99% or having 100% identity with the amino acid sequence SEQ ID NO: 13 and a complementary determining region 3 (CDR3) having at least 80%, 85%, 90%, 95%, 96%, 97%, 98%, 99% or having 100% identity with the amino acid sequence SEQ ID NO: 14.

"Polypeptide," "polypeptide fragment," "peptide" and "protein" are used interchangeably, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring.

Polypeptides can be prepared using any of a variety of well-known recombinant and/or synthetic techniques. Polypeptides contemplated herein specifically encompass the CARs of the present disclosure, or sequences that have deletions from, additions to, and/or substitutions of one or more amino acid of a CAR as disclosed herein.

An "isolated peptide" or an "isolated polypeptide" and the like, as used herein, refer to in vitro isolation and/or purification of a peptide or polypeptide molecule from a cellular environment, and from association with other components of the cell. Similarly, an "isolated cell" refers to a cell that has been obtained from an in vivo tissue or organ and is substantially free of extracellular matrix.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA.

The present invention also provides a vector comprising a nucleic acid molecule encoding the CAR of the invention, said vector is selected from a DNA, a RNA, a plasmid, a lentivirus vector, an adenoviral vector, or a retrovirus vector, preferably a lentivirus vector.

In some embodiments, the vector of the invention comprises a promoter, preferably an EF-1 alpha promoter.

Retroviruses are a common tool for gene delivery. In particular embodiments, a retrovirus is used to deliver a polynucleotide encoding a chimeric antigen receptor (CAR) to a cell. As used herein, the term "retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Thus, the T cells transduced with the vector of the invention can elicit a stable, long-term, and persistent CAR-mediated T-cell response.

In particular embodiments, the T cell is transduced with a retroviral vector, e.g., a lentiviral vector, encoding a CAR according to the present invention.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV); the caprine arthritis-encephalitis virus (CAEV); equine infectious anemia virus (EIAV); feline immunodeficiency virus (Hy); bovine immune deficiency virus (BIV); and simian immunodeficiency virus (SIV).

The term "lentiviral vector" refers to a viral vector or plasmid containing structural and functional genetic elements, or portions thereof, including LTRs that are primarily derived from a lentivirus.

"Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication.

In one embodiment, SIN vector backbones are preferred.

Preferably, the vector used further comprises a promoter, e.g. an EF-1 alpha promoter.

The term "promoter" as used herein refers to a recognition site of a polynucleotide (DNA or RNA) to which an RNA polymerase binds. An RNA polymerase initiates and transcribes polynucleotides operably linked to the promoter. In a particular embodiment, it may be desirable to express a polynucleotide comprising a CAR from a promoter that provides stable and long-term CAR expression in T cells and at sufficient levels to redirect the T cells to cells expressing the target antigen.

The present invention also provides a cell comprising a nucleic acid molecule encoding the CAR of the invention or the vector of the invention, the cell is preferably a T cell, e.g. human T cell, more preferably a CD8+ T cell, e.g. human CD8+ T cell. In a preferred embodiment, the cell of the invention (e.g. T cell) expresses the CAR of the invention at its membrane.

In particular embodiments, prior to in vitro manipulation or genetic modification of the immune effector cells described herein, the source of cells is obtained from a subject. In particular embodiments, the immune effector cells expressing the CAR of the invention at its membrane comprise T cells. T cells can be obtained from a number of sources including, but not limited to, peripheral blood mononuclear cells, bone marrow, lymph nodes tissue, cord blood, thymus tissue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation. In one embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing.

In certain embodiments, T cells are isolated from peripheral blood mononuclear cells by lysing the red blood cells and depleting the monocytes, for example, by centrifugation through a PERCOLL™ gradient. A specific subpopulation of T cells, expressing one or several markers like CD4 or CD8 can be further isolated by positive or negative selection techniques. For example, enrichment of a T cell population by negative selection can be accomplished with a combination of antibodies directed to surface markers unique to the negatively selected cells.

In some embodiments of the invention, a polynucleotide or cell harboring the polynucleotide of the present invention utilizes a suicide gene, including an inducible suicide gene to reduce the risk of direct toxicity (i.e. Graft versus host Diseases in allogeneic administration settings) and/or uncontrolled proliferation of gene modified cells. In specific aspects, the suicide gene is not immunogenic to the host harboring the polynucleotide or cell. A certain example of a suicide gene that may be used is inducible caspase-9 (iCASP9), thymidine kinase d'Herpes simplex (HSV-tk), CD20, truncated EGFR, caspase-8 or cytosine deaminase. Caspase-9 can be activated using a specific chemical inducer of dimerization (CID). Others systems may be activated by metabolizing prodrugs (Ganciclovir), or by binding antibodies (Rituximab, Cituximab).

Disclosed herein is a type of cellular therapy where T cells are genetically modified ex-vivo to express a CAR and the CAR T cell is infused to a recipient in need thereof. The infused cell is able to kill tumor cells in the recipient, preferably a human. Unlike antibody therapies, CAR T cells are able to replicate in vivo resulting in long-term persistence that can lead to sustained tumor control.

Moreover, CARs allow for the redirection and activation of effector T cells towards any cell surface molecule upon binding by the antibody derived receptor, and are independent of MHC restriction.

The genetically-modified T cells of the invention are constructed starting from the own T cells of the patient (autologous), but they can also originate from other allogenic donors to provide allogenic genetically-modified T cells in bone marrow or peripheral hematopoietic stem cell allograft context (Donor lymphocytes infusion). These T cells expressing a CAR molecule according to the invention are useful to treat a proliferative disease in a mammal, preferably a human, this disease being associated with cell surface IL-1RAP expression.

Preferably, these T cells express a CAR molecule comprising an antigen binding domain that is an anti-IL-1RAP scFv comprising an anti-IL-1RAP binding domain, a transmembrane domain of the CD28 protein, a costimulatory 4-1BB signaling domain, and a CD3 zeta signaling domain, wherein said anti-IL-1RAP binding domain comprises:
  (i) a light chain comprising a complementary determining region 1 (CDR1) having at least 80%, 85%, 90%, 95%, 96%, 97%, 98%, 99% or having 100% identity with the amino acid sequence SEQ ID NO: 6, a complementary determining region 2 (CDR2) having at least 80%, 85%, 90%, 95%, 96%, 97%, 98%, 99% or having 100% identity with the amino acid sequence SEQ ID NO: 7 and a complementary determining region 3 (CDR3) having at least 80%, 85%, 90%, 95%, 96%, 97%, 98%, 99% or having 100% identity with the amino acid sequence SEQ ID NO: 8, and
  (ii) a heavy chain comprising a complementary determining region 1 (CDR1) having at least 80%, 85%, 90%, 95%, 96%, 97%, 98%, 99% or having 100% identity with the amino acid sequence SEQ ID NO: 12, a complementary determining region 2 (CDR2) having at least 80%, 85%, 90%, 95%, 96%, 97%, 98%, 99% or having 100% identity with the amino acid sequence SEQ ID NO: 13 and a complementary determining region 3 (CDR3) having at least 80%, 85%, 90%, 95%, 96%, 97%, 98%, 99% or having 100% identity with the amino acid sequence SEQ ID NO:

The present invention also provides a cell according to the invention (e.g. a T cell) for use as a medicament.

The present invention also provides a cell according to the invention (e.g. a T cell) for use in the treatment of a proliferative disease in a mammal, preferably a human.

In some embodiments the proliferative disease is a disease associated with IL-1RAP expression.

The disease associated with IL-1RAP expression is preferably selected from a cancer or malignancy or a precancerous condition such as a myelodysplasia, a myelodysplastic syndrome or a preleukemia.

Adult tumors/cancers and pediatric tumors/cancers are also included.

More preferably, the disease is a hematologic cancer selected from the group consisting of one or more acute leukemias including B-cell acute lymphoid leukemia ("BALL"), T-cell acute lymphoid leukemia ("TALL"), acute lymphoid leukemia (ALL); one or more chronic leukemias including chronic myelogenous leukemia (CML) and chronic lymphocytic leukemia (CLL).

In a more preferred embodiment, the disease is a chronic myelogenous leukemia.

In first line, the treatment of CML involves the use of TKIs. However, once the treatment is stopped, more than half of the patients relapse, showing that the use of TKI does not cure the disease.

The T cell expressing the CAR molecule specific of IL-1RAP is therefore useful in a method to treat CML in a human, wherein the human has already been treated by at least one tyrosine kinase inhibitor (TKI).

Preferably, the T cell expressing the CAR molecule specific of IL-1RAP is therefore useful in a method to treat a proliferative disease in a mammal in association with at least one tyrosine kinase inhibitor (TKI).

The TKIs used may be Imatinib, Dasatinib, Nilotinib, Bosutinib and Ponatinib.

The T cell expressing the CAR molecule specific of IL-1RAP is therefore useful in a method to treat CML in a human, wherein the human has already received a graft-versus-leukemia, an allogenic stem cell transplantation or a donor lymphocytes infusion (DLI).

As used herein "treatment" or "treating," includes any beneficial or desirable effect on the symptoms or pathology of a disease or pathological condition, and may include even minimal reductions in one or more measurable markers of the disease or condition being treated, e.g., cancer. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

Thus, the present disclosure provides for the treatment or prevention of CML comprising administering to a subject in need thereof, a therapeutically effective amount of the T cells of the invention.

The T cells described herein may be administered either alone, or as a pharmaceutical composition in combination with diluents and/or with other components such as IL-2 or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also provides compositions, e.g. pharmaceutical compositions, comprising a cell, e.g. a T cell, according to the invention.

Compositions of the present invention are preferably formulated for parenteral administration, e.g., intravascular (intravenous or intraarterial), intraperitoneal or intramuscular administration.

"administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion.

In one embodiment, the CAR-modified T cells or the compositions contemplated herein are administered to a subject by direct injection into a tumor, lymph node, systemic circulation, or site of infection.

In one embodiment, the invention is useful to treat a subject diagnosed with a cancer, by removing immune effector cells from the subject, genetically modifying said immune effector cells with a vector comprising a nucleic acid encoding a CAR as contemplated herein, thereby producing a population of modified immune effector cells, and administering the population of modified immune effector cells to the same subject. In a preferred embodiment, the immune effector cells comprise T cells.

The quantity, frequency of administration and the sequence of the possible association with conventional CML treatment, including TKIs, will be determined by such factors as the condition of the patient, and the type and severity of the patient's disease, although appropriate dosages may be determined by animal models and finally by clinical trials.

A "therapeutically effective amount" of a genetically modified therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges.

The invention is further described in detail by reference to the following experimental examples. These examples are provided for purposes of illustration only, and are not intended to be limiting unless otherwise specified.

EXAMPLE 1: PATIENT'S SAMPLES, HEALTHY DONOR'S BLOOD SAMPLES, CELLS LINES

CML samples collection was established from patients, at diagnosis and follow-up after TKIs treatment. Peripheral blood mononuclear cells were isolated by Ficoll® gradient density centrifugation using Ficoll-Paque (Velizy-Villacoublay, France) from anonymous blood samples of healthy donors collected at the French Blood center (Besançon, France). Human tumors KU812 (CRL-2099), K562 (CCL-243) or epithelial 239T (CRL-3216), HT1080 (CCL-121) cell lines originate from ATCC® collection (LGC Standards, Molsheim, France).

EXAMPLE 2: MONOCLONAL ANTIBODY PRODUCTION

A mouse anti-hIL-1RAP monoclonal antibody was generated by standard hybridoma technique.

Briefly, BALB/c mice (5 weeks, Charles River) were immunized either by foot pad (n=3) or intraperitoneally (n=5) with a recombinant fusion protein consisting of the extra cellular part of IL-1RAP (NM_002182.2, NCBI) and the Fc-part of human IgG1 (R&D Systems, Lille, France). Lymph nodes or spleens cells and blood samples were harvested and cells were fused with the mouse myeloma cell line, then screened by FACS analysis (Becton Dickinson), against IL-1RAP-positive (KU812) and –negative (Raji, KG1) cell lines.

Screening of hybridoma allowed to select 5 monoclonal antibodies subclones that discriminate IL-1RAP positive (KU812 or KG-1 respectively AML or Phi$^+$p$^{210}$ CML) from negative cell lines (Tom-1, NALM-20, Jurkat or Raji, respectively Phi+$^{p190}$ B-ALL, Phi-B-ALL, T-ALL or Burkitt's lymphoma).

Molecular Characterization of Antibodies

Molecular characterization was performed by Sanger sequencing of cloned PCR products amplification obtained with degenerated primers specific of the FR1 and constant regions of the heavy and light chains according to the protocol of Wang. Z., et al (J. Immunol. Methods, 2000; 233, pp 167-77). Identification of V-D-J-C gene rearrangement and CDR3 region was obtained after alignment of consensus nucleotide sequences against the IMGT® database using V-QUEST online tool according to Brochet X., et al. (Nucleic Acids Res., 2008, 36, pp 503-8). Molecular Sanger sequencing showed that all of the 5 monoclonal antibodies are identical and share the same CDR3 nucleotide sequences. The monoclonal antibody subclone (#E3C3) was chosen, since it gave the highest relative fluorescence intensity (RFI) by cytometry.

Selected antibody (clone #E3C3) was characterized by western blotting, ELISA against recombinant IL-1RAP protein, immunohistochemistry, confocal microscopy, tissue micro array (TMA) from normal tissues (FDA normal human organ tissue array, 99 cores/33 sites/75 cases) and primary samples of CML patients.

Western Blotting of Subcellular Fractions

Whole-cell, subcellular or secreted protein fractions of cells listed in example 1 were obtained after sonication and suspended in RIPA lysis and extraction buffer (ThermoFisher Scientific) supplemented with a protease inhibitor cocktail (complete Mini EDTA-free; Roche, Switzerland). Transfected HT1080 cell line with IL-1RAP cDNA variant 1 (NM_002182.2, NCBI) was used as control. Actin was revealed as a protein loading control. Transferred proteins on PDVF membranes were probed overnight with either primary IL-1RAP #E3C3 (diluted at 1:10$^3$), CD3zeta (BD Pharmigen, clone #8D3) or β-actin (1:10$^3$, clone AC15, #A5441, Sigma-Aldrich) respectively for IL-1RAP, CAR or β-actin expression. Immunodetection staining was performed with a secondary polyclonal antibody sheep anti-mouse IgG (#515-035-062, Jackson, USA). Detection was performed with a camera and Bio-1D software (Vilber-Lourmat, Collegien, France). The use of #E3C3 monoclonal antibody in western blot reveals KU812 (FIG. 1).

In Vitro Detection of Recombinant IL-1RAP Protein Via ELISA.

Anti-human Fc antibody was coated on a bottom of a plastic ELISA plate. IL-1RAP protein loaded on human antibody was probed with the murine and human IL-1RAP (#E3C3) antibody, revealed then by an anti-mouse FC antibody coated with horseradish peroxidase (HRP).

The ELISA confirms that #E3C3 monoclonal antibody recognize the IL-1RAP recombinant protein (FIG. 2).

Flow Cytometry Analysis on Primary Cells from CML Patients.

Hematopoietic stem cells from CML patients were tracked using a panel of CD45, CD34, CD38, CD33, CD133, CD117 including murine Alexa Fluor® 488 labelled IL-1RAP antibody clone #E3C3. Transduced cells were stained using a panel of antibodies including CD3, CD4, CD8, and CD19 in order to differentiate helper or cytotoxic GMTC. Naïve, central or memory T cells subsets were analyzed using a panel of CD45RA, CD62L, CD95, CCR7 monoclonal antibodies. Cells were collected using a FACSCANTO™ II cytometer (BD Biosciences, Le Pont de Claix, France) and analyzed using the DIVA 6.1 software (BD Biosciences, Le Pont de Claix, France).

Immunophenotyping on peripheral blood or bone marrow of 2 CML-positive patients without or after Imatinib (TKI) treatment has been performed. IL-1RAP (#E3C3) was used in combination with CD34$^+$ and CD38$^-$ fluorescent staining. Fluorochrome-conjugated isotype control monoclonal antibodies from the different monoclonal antibodies were systematically used.

Integration of #E3C3 monoclonal antibody in a panel of antibodies allowed to discriminate IL-1RAP+ leukemia expressing stem cells CD34$^+$CD38$^+$ or CD34$^+$CD38$^-$ subpopulations in bone marrow or peripheral blood of patient at diagnosis or after 12 months of Imatinib (FIG. 3).

Confocal Microscopy

Confocal microscopy was assessed on KU812 and Raji cells lines concentrated on slides (Superfrost™ Plus, 4951PLUS4, ThermoFisher Scientific) by Cytospin. Briefly, the cells were stained with Fluorescent monoclonal antibodies: anti murine Fc-IgG; IL-1RAP (#E3C3) and were analyzed with an Olympus BX51 microscope equipped with a QImaging Retiga 2000R camera. Digital images were acquired using the 40× objective and digitalized with Image-Pro Plus (version 6.0, Media Cybernetics). Counterstaining was performed by nuclear stain DAPI (2-(4-Amidinophenyl)-6-indolecarbamidine dihydrochloride, Sigma-Aldrich-France) and superposed to fluorescent staining.

Confocal microscopy clearly show a cell membrane staining corresponding to the IL-1RAP expression (FIG. 4).

Detection In Situ

In order to study specific or non-target tissue binding, FDA standard frozen tissue arrays, including 90 tissue cores (30 organs) of 3 individual donors per organ (US Biomax, Rockville, United States) were incubated as previously described. Immunostaining was detected using UltraView Universal DAB Detection Kit (Ventana, USA). Images were acquired and analyzed with NDP.view 2 software. High IL-1RAP (KU812) or negative (Raji) expressing cell lines were respectively used as positive or negative controls. The staining intensity was graduated as follows: negative (0), weak staining (1+), moderate staining (2+), or strong staining (3+). High IL-1RAP (KU812) or negative (Raji) expressing cell lines were respectively used as positive or negative controls.

IL-1RAP expression has been investigated using #E3C3 monoclonal antibody. Staining was detected in only 6 tissues as Lymph node, colon, small intestine, placenta, stomach and prostate, mainly epithelial or endothelial cells at various intensity (FIG. 5).

EXAMPLE 3: LENTIVIRAL CONSTRUCTS

Based on molecular sequencing of VDJ or VJ rearrangements and CDR3 nucleotide sequence determination, CAR lentiviral construct (pSDY-iC9-IL-1RAPCAR-dCD19) was prepared by cloning the synthetically produced single chain Fragment variable (scFv) derived from the #E3C3 IL-1RAP hybridoma of example 1 into the SIN-pSDY backbone (Rossolillo P, Winter F, Simon-Loriere E, Gallois-Montbrun S, Negroni M. Retrovolution: HIV-driven evolution of cellular genes and improvement of anticancer drug activation. PLoS Genet. 2012; 8(8):e1002904).

Briefly, a SIN lentiviral construct carrying a safety cassette iCASP9, the single chain fragment variable of #E3C3 monoclonal antibody and a cell surface expressed marker ΔCD19 for monitoring and potential cell selection has been constructed. All of these 3 transgenes are separate by 2A peptide cleavage sequences and under control of EF1 promoter and SP163 enhancer sequence (part of the 5'UTR of the mouse VEGF gene, GenBank accession #U41383).

As seen in FIG. 6, the construct carries 3 different parts as a suicide safety cassette iCASP9 (chemical inducible Caspase 9), the IL-1RAP CAR and a cell surface and selection marker as ΔCD19 (CD19 truncated of the intracellular part avoiding signaling), separated by 2 different 2A ribosomal skip sequences (P2A and T2A) and under control of EF1a (Elongation Factor 1 promotor alpha) promoter and of the SP163 enhancer. The scFv, constituted of the variable regions of the Heavy (VH) and Light (VL) sequence chains of #E3C3 immunoglobulin is cloned in frame with the CD28-4.1BB-CD3z signaling chain and under control of the EF1a promoter and the SP163 enhancer. The IL-1RAP CAR contains of single chain variable fragments (scFv), associated with a leader sequence (L), tagged with Human influenza hemagglutinin (HA) and connected through a hinge region to T cell activating domain consisting of 2 co-stimulatory domains (modified transmembrane and intracellular signaling CD28 and 4-1BB) and the CD3z intracellular signaling domain. Mock T consists of the same construct without IL-1RAP scFv.

EXAMPLE 4: GENERATION OF IL-1RAP CART CELL

CD3+ T lymphocytes obtained from healthy donors peripheral blood mononuclear cells were activated with anti-CD3/CD28 beads (Life Technologies, France) according to the manufacturer's instructions, and then isolated over a magnetic column (MACS®, Miltenyi Biotec, Paris, France). On day 2, activated T cells were transduced by spinoculation, in contact of the supernatant (SN), at 2000 g for 90 min at 10° C. Transduction efficiency was determined by performing flow cytometric analysis to identify ΔCD19 cell surface marker expression. Four days after transduction, CD19 positive cells labeled with CD19 microbeads (Miltenyi Biotec, Paris, France) were magnetically separated using a MACS Column. The isolated CD19 expressing cells were expanded in complete X-vivo™ medium (Lonza, Bale, Suisse) containing 500 UI/mL rhIL-2 (Proleukin; Novartis), supplemented with 8% human serum and cryopreserved. Experimentally, we used TransAct™ Cell Reagent and Tex-MACS™ Medium (Miltenyi Biotec, Paris, France) supplemented with Human IL-2; IL-7, IL-15 or IL-7+IL-15.

EXAMPLE 5: LENTIVIRAL TRANSDUCTION OF DONOR T CELLS

Lentiviral vector supernatant stocks were produced by transient co-transfection of subconfluent 293T cells using CaCl2) method with helper plasmids encoding vesicular stomatitis virus (VSV) envelope (pMDG), and the GAG/POL (psPAX2) packaging plasmids (Addgene, respectively #12259 and #12260, Trono et at, Lausanne, Switzerland). Viral supernatant was harvested 48 and 72 hours later, concentrated using PEG and low speed centrifugation (3000 g, overnight), then stored at −80° C. until use. The same lentiviral construct (Mock) without IL-1RAP scFv was used as control. Titration of the lentiviral supernatant was established by 293T permissive cells transduction using serial dilution of SN.

Transduction efficiency was measured by flow cytometry. Multiplicity of infection (MOI) was deducted from supernatant titration according to the number of starting cells.

In vitro production process with lentiviral supernatant allows to transduce primary T cells respectively at MOI of 2 for Mock or CAR IL-1RAP supernatant.

Western Blot Analysis of IL-1RAP CAR Expression.

Whole protein lysate or protein extracted from membrane or cytoplasm cellular subfractions (obtained after ultracentrifugation) of IL-1RAP transduced T cells were probed with a mouse anti-human CD3z antibody. Western blotting on subcellular fractions showed that the IL-1RAP CAR is associated with CD3z signaling (signal at 55KDa compared to the expected endogenous CD3z signal at 16KDa) (FIG. 7).

Analysis by Flow Cytometry

CAR expression at T cell surface analyzed using the recombinant IL-1RAP biotinylated protein and revealed by flow cytometry using a secondary anti-biotin antibody (Miltenyi Biotec Clone #Bio3-18E7). CEM cell line or primary T cells were transduced either with Mock or CAR IL-1RAP. Cells were then incubated in presence of increasing amount of recombinant IL-1RAP labelled with biotin. Staining was performed with an anti-biotin fluorescent antibody and analyzed by flow cytometry. Percentage of Biotin+/CD19+ CEM or T-cells were plotted against amount of labelled biotin recombinant protein. Dot plots of cytometry analyze were provided for representative staining, including maximum. Untransduced cells (CO) or Mock T cells are used as control.

Additional analysis using serial dilution of biotinylated IL-1RAP protein (from 20 ng to 2.4 pg/ml) and FACS analysis allow to detect either IL-1RAP CAR transduced CEM T cell line or primary T-cells. Single experiment allow to show that different amounts of recombinant protein, as 1.25 ng and 0.15 ng are respectively required for recruiting maximum of CEM (85.8%) or primary (68.5%) GMTC (FIG. 8).

More CAR are expressed at the cell surface of CEM than primary T cells. Moreover, addition of high amount (1000 time >plasmatic concentration) of cold recombinant IL-1RAP protein in E:T coculture lead to a significate inhibition of the effector cytotoxicity.

These experiments confirm that CAR is addressed at the cell surface and that there is a CAR specific recognition and binding of IL-1RAP protein.

EXAMPLE 6: EFFICIENCY OF THE SAFETY SUICIDE GENE ICASP9 CASSETTE

Transduced (IL-1RAP CAR 293T) or untransduced (293T) cells were cultured in media alone (-Chemical Inducer Dimerizer (CID)) or media containing 20 nM of CID AP1903 for 24 h. Light microscopy allow to image the presence and architecture of the live or death cells in culture(x40).

By optical microscopy, it can be shown that 293T cells culture transduced by IL-1RAP CAR is sensitive to the CID (FIG. 9).

Flow cytometry analysis after CID exposure (20 nM, 24 h) or not (light grey) on untransduced T cells (CO) and on GMTC cells mixture, expressing or not IL-1RAP CAR. $CD3^+/CD19^+$ staining allow to discriminate GMTC expressing CAR from the others.

Untransduced (CO) or IL-1RAP CART Cells were both exposed to medium alone or medium +CID (20 nM, 24 h).

Precise cell death was first assessed by flow cytometry after Annexin-V/7-AAD gating according to the manufacturer's instructions (Beckman Coulter, IM3614). Fluorescence analysis was gated on $CD3^+/CD19^+$ positive cells. The quantification was determined with after acquiring 5000 fluorescent beads. Killing efficiency was normalized against control cells (untreated cells). Cell killing was calculated as follows: % Dead cells=[1−(absolute number of viable cells in AP1903−treated cells/absolute number of viable cells in untreated cells)]×100·24 h or 48 h CO or IL-1RAP CART (gated on CD3+/CD19+) cells CID exposure. Results are showed as mean±SD from 3 independent experiments. ***: p<0,001 (FIG. 10).

Cytometry analysis show that after 24 h CID exposure of a mixed population of T cells expressing ($CD19^+$) or not ($CD19^-$) IL-1RAP CAR, only the $CD19^-$ CD3+ cells persist. More precisely, using a quantitative AnnV/7AAD assay of apoptosis, we showed that 84.11% and 88.93% of IL-1RAP CART cells are eliminated after 24 h or 48 h CID exposure compared respectively to untransduced T cells (CO) (1.28% and 6.13% respectively at 24 h or 48 h) (p<0.001, n=3).

EXAMPLE 7: IL-1RAP DEPENDENT PROLIFERATION AND CYTOKINE SECRETION OF IL-1RAP CAR EXPRESSING T-CELLS

To analyze proliferative and more widely functional properties of IL-1RAP CART cells, in addition to naturally IL-1RAP expressing cell line KU812, a deficient MHC class I cell line K562, expressing either the membrane (isoforms 1) or the soluble (isoform 3) of IL-1RAP respectively translated from variants 1 (v1) or 5 (v5) transcripts has been generated. For producing membrane (mb) or soluble (s) IL-1RAP expressing cell line, K562 cells were transfected respectively with variant 1 (isoform 1, NM_002182.2) or variant 5 (isoform 2, NM_001167930) ORF clones (pCMV6-AC-GFP vector, Origen or pEZ-M61, GeneCopoeia). Stable mb- or s-IL-1RAP expressing K562 cells were then transduced with the pLenti CMV V5-LUC Blast (Addgene, plasmid #21474).

A Western blotting analysis has been performed on these cells. Briefly, whole-cell (Total cellular) or secreted protein (medium supernatant) fraction were obtained from transfected K562 cell line, after sonication in RIPA buffer supplemented with a protease inhibitor cocktail (complete Mini EDTA-free; Roche, Bale, Switzerland). Twenty µg of proteins were SDS-PAGE electrophoresed, then electrotransfered onto PVDF membranes. Membranes were probed overnight with primary IL-1RAP #E3C3 (diluted at $1:10^3$) for IL-1RAP expression. β-actin mAb staining ($1:10^3$, clone AC15, #A5441, Sigma-Aldrich) was used as protein loading evaluation. Immunodetection staining was performed with a secondary polyclonal antibody sheep anti-mouse IgG (#515-035-062, Jackson). chemiluminescence detection was assessed with a camera and Bio-1D software (Vilber-Lourmat, Collegien, France).

By Flow cytometry and western blotting, these experiments confirm that isoform 1 (v1) is well expressed at the cell surface and that the isoform 3 (v5) is detected in the culture supernatant of K562-v5 but not of −v1 (FIG. 11A and B).

K562-v1 (dark) and KU812 (light) were stained with IL-1 RAP antibody (Red histograms) and compare to unlabeled cells (blue histograms). Relative Fluorescent intensity provide by the software is reported.

Interestingly, IL-1RAP expression of transfected K562-v1 is higher than in naturally IL-1RAP expressing KU812 cell line [Ratio Fluorescent Intensity (RFI)=10.57 versus 33.46]. (FIG. 11A and B).

EXAMPLE 8: PROLIFERATIVE CAPABILITY OF IL-1RAP CART CELLS

To determine the proliferative capability of IL-1RAP CART cells triggered by the IL-1RAP target expressing cells, we performed a co-culture (Effector-Target ratio, E:T=1:1) of CFSE stained CO, mock or IL-1 RAP CART cells in presence of K562, K562-v1, −v5 or KU812 cell lines.

Compared to CO or Mock cells, effector IL-1RAP CART cells divided significantly only in response against presence of IL-1RAP cell surface expressing K562-v1 (76.1%±10.9) and KU812 cells (81.6%±6.16), but at lowest level against K562-v5 (27.3%±9.03) or medium only (18.8%±7.02). (p<0.001, n=4)

In the same manner, but at a ratio E:T=1:5, we assessed, by intracellular IFN-γ production staining, how CART cells are able to produce IFN-γ in presence of IL-1RAP$^+$ targets cells.

IL-1RAP CART $CD8^+$ or $CD8^-$ cells, but not CO or Mock cells produced IFN-γ and exclusively against IL-1RAP expressing target cells K562-v1 ($CD8^+$: 23.7±0.71% and $CD8^-$: 14.8±3.58%) and KU812 ($CD8^+$: 22.3±2.39% and $CD8^-$: 13.1±2.79%) (p<0.001, n=4) (FIG. 12).

EXAMPLE 9: PROFILES OF CYTOKINES

To determine the profile of cytokines produced by CART cells, the human Th1/Th2/Th17 Cytokines Bead Array (CBA) Kit (BD Biosciences) allowing quantification of human IL-2, IL-4, IL-6, IL-10, TNF-α, IFN-γ, and IL-17A secretion has been used in accordance with the manufacturer's instruction. Briefly, supernatants of overnight culture of $1.10^5$ CART cells, in presence of target cells (ratio 1:1) or not (control), were incubated 3 h, with beads and PE-conjugated anti-cytokine antibodies. Beads were washed and acquired by standardized flow cytometry assay. Data were analyzed using FCAP Arrayä Software Version 3.0 (BD Biosciences). The supernatant collected from target cells only has been used as a control. Representative capture beads fluorescence analysis of culture supernatant of untransduced, Mock- or CAR IL-1RAP T cells in presence or not (Medium, PMA/Iono) of targets expressing (K562-IL-1RAP$^+$v1, KU812) or not (K562) IL-1RAP. For co-culture of IL-1RAP positive cells culture supernatant with effectors, supernatant were diluted at 1/3. Medium and PMA/Iono are use as negative and positive controls respectively.

Finally, in addition to confirm that stimulation of IL-1RAP CART cells display a Th1-like cytokines profile secretion, Th1/Th2/Th17 cytokines in the supernatant after co-culturing with CO, Mock or CART cells (E:T=1:1) has been measured.

Only IL-1RAP cell surface expressing K562-v1 and KU812 cells are able to trigger cytokines secretion with robust IFNg and IL-2 secretion, moderate TNFa, and low IL-4, IL-6 and IL-10 but not IL-17 secretion, directing rather to a specific Th1 profile (FIG. 13).

EXAMPLE 10: IL-1RAP-DEPENDANT CAR CYTOTOXICITY AND LYSIS OF IL-1RAP EXPRESSING TUMOR TARGET CELL LINES

T-cell mediated cytotoxic activity was analyzed with a CD107 degranulation assay. Cell cytotoxicity of CAR-T cells against live tumor cells was assessed by incubation, for 20-24 h, at different E:T cell ratio. CD107a&b degranulation assay applied on IL-1RAP CART cells, cocultured, at an E:T ratio=1:5, against IL-1RAP$^+$ (K532-V1, KU812) expressing target cells show a significant cell surface mobilization of CD107a&b in both the CD8$^-$ (mainly CD4+) and CD8$^+$ compartments of IL-1RAP-specific T cells, but not against cell surface IL-1RAP$^-$ (K562, K562-v5) expressing cells, while Mock or untransduced (CO) cells from the cells donor showed no appreciable degranulation (p<0.001, n=4) (FIG. 14).

To determine the IL-1RAP dependent cytolytic potency of IL-1RAP CAR expressing T cells in-vitro, we used fluorescent (eFluor) and 7-AAD staining, in order to discriminate respectively CART cells and living cells.

A statistically significant lytic activity characterized by the disappearance of cells in the gate 7-AAD$^-$/eFluor$^-$ between IL-1RAP$^+$ (K562-v1 and KU812) target cells and IL-1RAP$^-$ (K562, K562-v5) target cells (p<0.001, n=4) can be shown. Untransduced or mock-transduced T cells were used as control (FIG. 15).

EXAMPLE 11: XENOGRAFT MURINE MODELS—IN VIVO STUDIES (FIG. 16)

NSG (NOD.Cg-Prkdcscid Il2rgtm1WjI/SzJ) mice (Charles River, France) were transplanted with Luc+, IL-1RAP+ tumor cell lines, with injection or not of effector CAR T cells. In addition to mice survival, circulating CART cell and tumor burden were analyzed every week either by cytometry or bioluminescence analysis.

Briefly, mice were sub-lethally irradiated at the dose of 3.5Gy (n=5/group) 24 hours before transplantation. $2\times10^6$ K562-v1, IL-1RAP$^+$, Luciferase$^+$, GFP$^+$ expressing cell line (K562-v1$^{IL\text{-}1RAP+/GFP+/Luc+}$), were then transplanted into 6-8 weeks-old NOD.Cg-Prkdcscid Il2rgtm1Wjl/SzJ (NSG) mice (The Jackson Laboratory, Bar Harbor, ME) using tail-intravenous (i.v) injection. $1\times10^{E6}$ to $5\times10^{E6}$ MockT or IL-1RAP CART cells were injected once i.v, 4 days after tumor injection. A group of K562-v1$^{IL\text{-}1RAP+/GFP+/Luc+}$ injected mice but untreated by T cells was used also as controls. For tracking K562-v1$^{IL\text{-}1RAP+/GFP+/Luc+}$ tumor burden, mice were weekly injected intraperitoneally with 50 mg/g D-luciferin (Promega, Lyon, France) 10 min prior imaging on a NightOwl (Berthold Technologies, Thoiry, France), under isoflurane anesthesia. The ability of IL-1RAP CART-cells to eliminate IL-1RAP expressing cells in vivo has been evaluated.

The results show that following tumor engraftment (D4), IL-1RAP CART-cells (E:T=1:1) are allowed to target K562-v1$^{IL\text{-}1RAP+/Luc+}$ tumor, until notice a decrease of the size (D4 to D9) going to its complete elimination (at >D9).

In contrast, tumor progression in un- or Mock T-cells treated mice leading to the death of mice (2/3 in both groups respectively at D28) is noticed, while no mice die in the CART cells treated group. Interestingly, tumors continue to growth in absence of CART-cells in surviving mice of un- or Mock T-cells treated groups.

EXAMPLE 12: IN VITRO CYTOTOXICITY AGAINST PRIMARY IL-1RAP-EXPRESSING CELLS FROM CML PATIENTS

From a primary TKI-resistant CML patient (always with BCR-ABL(IS) ratio >10%) to five lines of treatment with four TKIs (FIG. 17 top) for a period of 4 years, we were able to produce CART cells with a transduction efficiency of 95.5% (FIG. 17 bottom). IL-1RAP CART cells exhibited dose-dependent cytotoxic activity against IL-1RAP+ KU812 cells with 95% efficiency at an E:T ratio of 3:1 compared to an allo-reactive cytotoxicity of 18% and 21% for CO or Mock T cells, respectively (FIG. 18), which was comparable to IL-1RAP CART cells produced from healthy donors. Moreover, co-culture of autologous IL-1RAP CART cells against CML patient PBMCs exhibited specific lysis (76.65±9.2% for IL-1RAP CART cells compared to 4.16±4.3% and 2.78±1.72% for CO or Mock T cells, respectively) of IL-1RAP+/CD34+ cells after 24 h (FIG. 19).

Moreover, autologous IL-1RAP CART cells produced (transduction efficiency: 85.33±8.8%) from CML patients (n=3) under long-term treatment, including TKIs, or free of treatment (FIG. 21), and directed against their respective initial long-term cryopreserved (>20 years) peripheral blood stem cell autograft, killing the CD34+/IL-1RAP+ cells with an efficiency of 79.78±10.7% (FIG. 20).

EXAMPLE 13: IL-1RAP-CART CELLS SECURED BY AN ICASP9 SAFETY SWITCH HAVE NO MAJOR DELETERIOUS EFFECT ON HEALTHY HEMATOPOIETIC CELLS

Figure 22A:
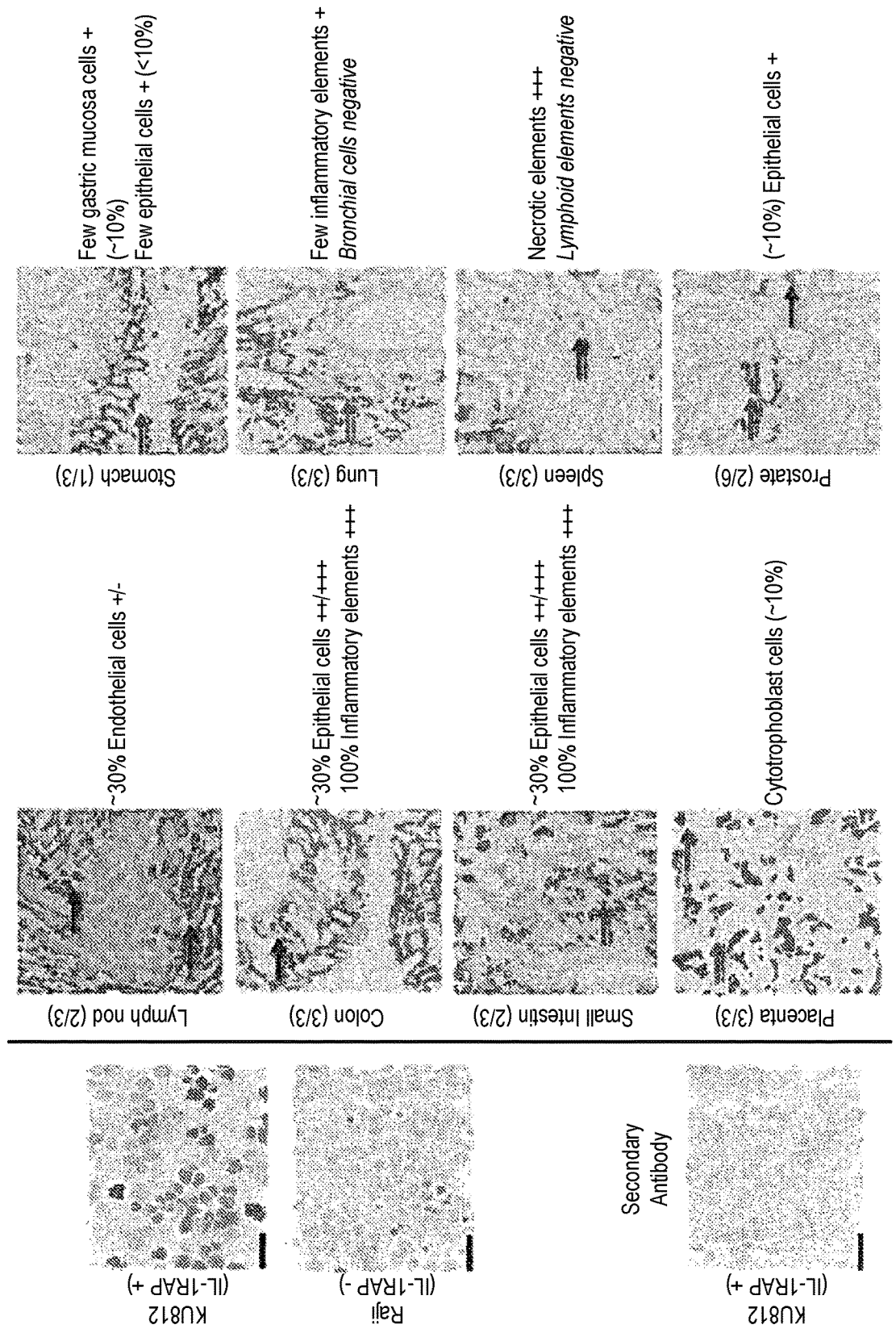
Figure 22B:
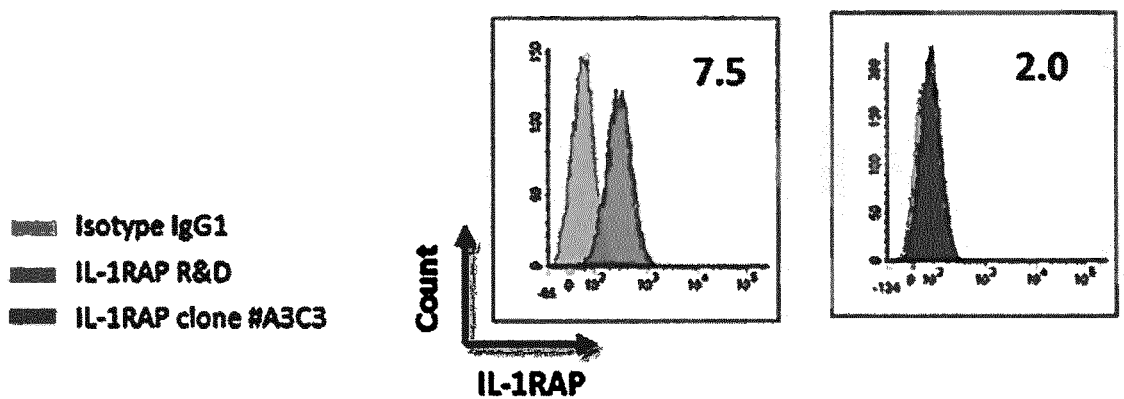

In order to predict off-target toxicity, we used the #A3C3 mAb to investigate IL-1RAP expression using a tissue macroarray (TMA) of 30 normal human tissues. Staining was detected at various intensity levels, excluding inflammatory or necrotic elements, in only six tissues: lymph node, prostate, skeletal muscle, stomach, colon and small intestine, and pancreas (FIG. 22A and Table 2). Interestingly, the microvascular HMEC-1 endothelial cell line was not recognized by our #A3C3 IL-1RAP mAb (FIG. 22B), whereas the R&D IL-1RAP mAb (R&D Systems—Ref #89412) clearly detects cell surface expression, suggesting recognition of a different epitope.

Figure 23E:
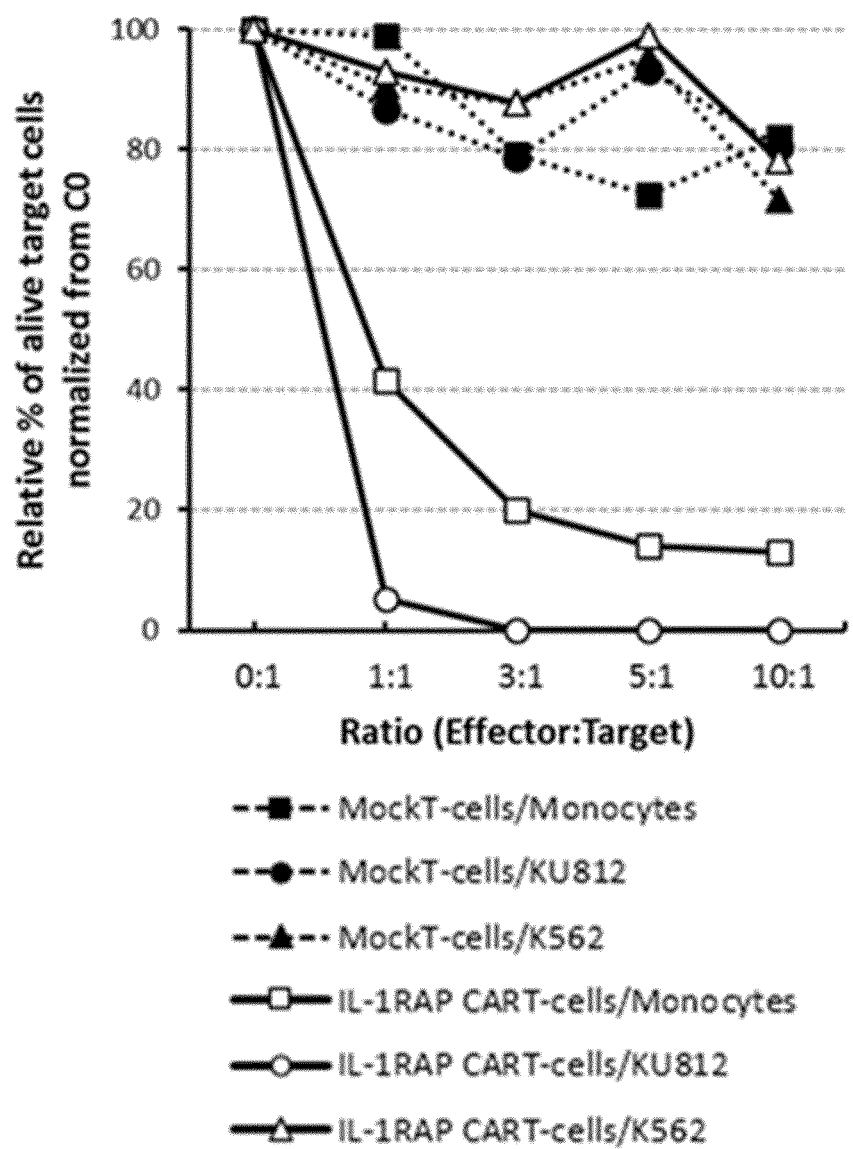

Regarding targeting of the healthy hematopoietic system, if mAb #A3C3 did not detect HSCs in bone marrow (RFI<1.2, n=5) from healthy donors (FIG. 23A, C) or normal cord blood (FIG. 23B, C), we noted weak staining (RFI<2) of the monocyte subpopulation in 2/5 peripheral blood and 3/5 bone marrow from healthy donors (FIG. 23A). Next, we studied the in vitro sensitivity of monocytes by co-culturing PBMCs and autologous CART cells at various E:T ratios. At an E:T ratio of 1:1, only some of the monocytes were targeted, leaving 41.45% of monocytes alive (FIG. 23D, right, Table 3), whereas lymphocytes, granulocytes, and the K562 IL-1RAP-negative cell line were not affected (FIG. 22D), even at superior E:T ratios. Interestingly, at this E:T ratio, 94.77% of leukemic cells were killed (FIG. 23E).

TABLE 2

IL-1RAP (mAb#A3C3) immunostaining of normal tissues

| Tissues (replicates) | Staining intensity (0 to 3+) | Comments |
|---|---|---|
| Lymph node 1 | 2+ | ~30% of endothelial cells |
| Lymph node 2 | | |
| Lymph node 3 | 1+ | ~30% of endothelial cells |
| Skeletal muscle 1 | 1+ | ~10% of endothelial cells |
| Skeletal muscle 2 | 0 | |
| Skeletal muscle 3 | 0 | |
| Prostate 1 | 1+ | ~10% of endothelial cells |
| Prostate 2 | 1+ | ~10% of endothelial cells |
| Prostate 3 | 0 | |
| Prostate 4 | 0 | |
| Prostate 5 | 0 | |
| Prostate 6 | 0 | |
| Kidney 1 | 0 | |
| Kidney 2 | 0 | |
| Kidney 3 | 0 | |
| Liver 1 | 0 | |
| Liver 2 | 0 | |
| Liver 3 | 0 | |
| Lung 1 | 2+ | |
| Lung 2 | 2+ | Few inflammatory elements |
| Lung 3 | 2+ | |
| Stomach 1 | 1+ | Few gastric mucosa cells (~10%); few epithelial cells <10% |
| Stomach 2 | 0 | |
| Stomach 3 | 0 | |
| Esophagus 1 | 0 | |
| Esophagus 2 | 0 | |
| Esophagus 3 | 0 | |
| Heart 1 | 0 | |
| Heart 2 | 0 | |
| Heart 3 | 0 | |
| Colon 1 | 3+ | |
| Colon 2 | 3+ | Epithelial cells (~30%); inflammatory elements (100%) |
| Colon 3 | 3+ | |
| Small intestine 1 | 2+ | Epithelial cells (~30%); inflammatory elements (100%) |
| Small intestine 2 | 0 | |
| Small intestine 3 | 1+ | Epithelial cells (~30%); inflammatory elements (100%) |
| Peripheral nerve 1 | 0 | |
| Peripheral nerve 2 | 0 | |
| Peripheral nerve 3 | 0 | |
| Smooth muscle 1 | 0 | |
| Smooth muscle 2 | 0 | |
| Smooth muscle 3 | 0 | |
| Cerebellum tissue 1 | 0 | |
| Cerebellum tissue 2 | 0 | |
| Cerebellum tissue 3 | 0 | |
| Ovary 1 | 0 | |
| Ovary 2 | 0 | |
| Ovary 3 | 0 | |
| Pancreas 1 | 1+ | |
| Pancreas 2 | 1+ | Cytotrophoblast cells (~10%) |
| Pancreas 3 | 1+ | |
| Salivary gland 1 | 0 | |
| Salivary gland 2 | 0 | |
| Salivary gland 3 | 0 | |
| Pituitary gland 1 | 0 | |
| Pituitary gland 2 | 0 | |
| Pituitary gland 3 | 0 | |
| Placenta 1 | 0 | |
| Placenta 2 | 0 | |
| Placenta 3 | 0 | |
| Skin 1 | 0 | |
| Skin 2 | 0 | |
| Skin 3 | 0 | |
| Spinal cord 1 | 0 | |
| Spinal cord 2 | 0 | |
| Spinal cord 3 | 0 | |
| Spleen 1 | 3+ | |
| Spleen 2 | 3+ | Necrotic elements |
| Spleen 3 | 3+ | |
| Skeletal muscle 1 | 0 | |
| Skeletal muscle 2 | 0 | |
| Skeletal muscle 3 | 0 | |
| Testis 1 | 0 | |
| Testis 2 | 0 | |
| Testis 3 | 0 | |
| Adrenal gland 1 | 0 | |
| Adrenal gland 2 | 0 | |
| Adrenal gland 3 | 0 | |
| Thyroid gland 1 | 0 | |
| Thyroid gland 2 | 0 | |
| Thyroid gland 3 | 0 | |
| Ureter 1 | 0 | |
| Ureter 2 | 0 | |
| Uterine cervix 1 | 0 | |
| Uterine cervix 2 | 0 | |
| Uterine cervix 3 | 0 | |

TABLE 3

Percentage of alive cells in different subpopulations according co-culture with different ratio of E (MockT-cells or IL-1RAP CART-cells):T.

| E:T | Subpopulations | Mock T-cells | IL-1RAP CART-cells |
|---|---|---|---|
| [1:1] | Lymphocytes (%) | 90.79 | 75.43 |
| | Monocytes (%) | 98.71 | 41.45 |
| | Granulocytes (%) | 93.27 | 89.31 |
| [3:1] | Lymphocytes (%) | 84.98 | 94.31 |
| | Monocytes (%) | 79.19 | 19.94 |
| | Granulocytes (%) | 79.32 | 96.14 |
| [5:1] | Lymphocytes (%) | 89.1 | 97.51 |
| | Monocytes (%) | 72.31 | 13.93 |
| | Granulocytes (%) | 77.15 | 90.19 |
| [10:1] | Lymphocytes (%) | 96.13 | 98.61 |
| | Monocytes (%) | 82.03 | 13.05 |
| | Granulocytes (%) | 82.87 | 98.46 |

These results were confirmed in vivo in an hCD34-engrafted murine model (hu-NOG), in which we demonstrated that, although monocytes decreased on day 15 (41±25%, n=3, p=n.s), that other human immunocompetent cells derived from hCD34+ cells were not affected by CART cells (FIG. 24). Hematopoietic stem cell culture assay after in vitro co-culture of healthy CD34+ cord blood HSCs with autologous CART cells (n=3) confirmed that HSCs were not affected (FIG. 25). These results agree with IL-1RAP CART cell immunotherapy being associated with few side effects on the hematopoietic system.

Figure 23F:
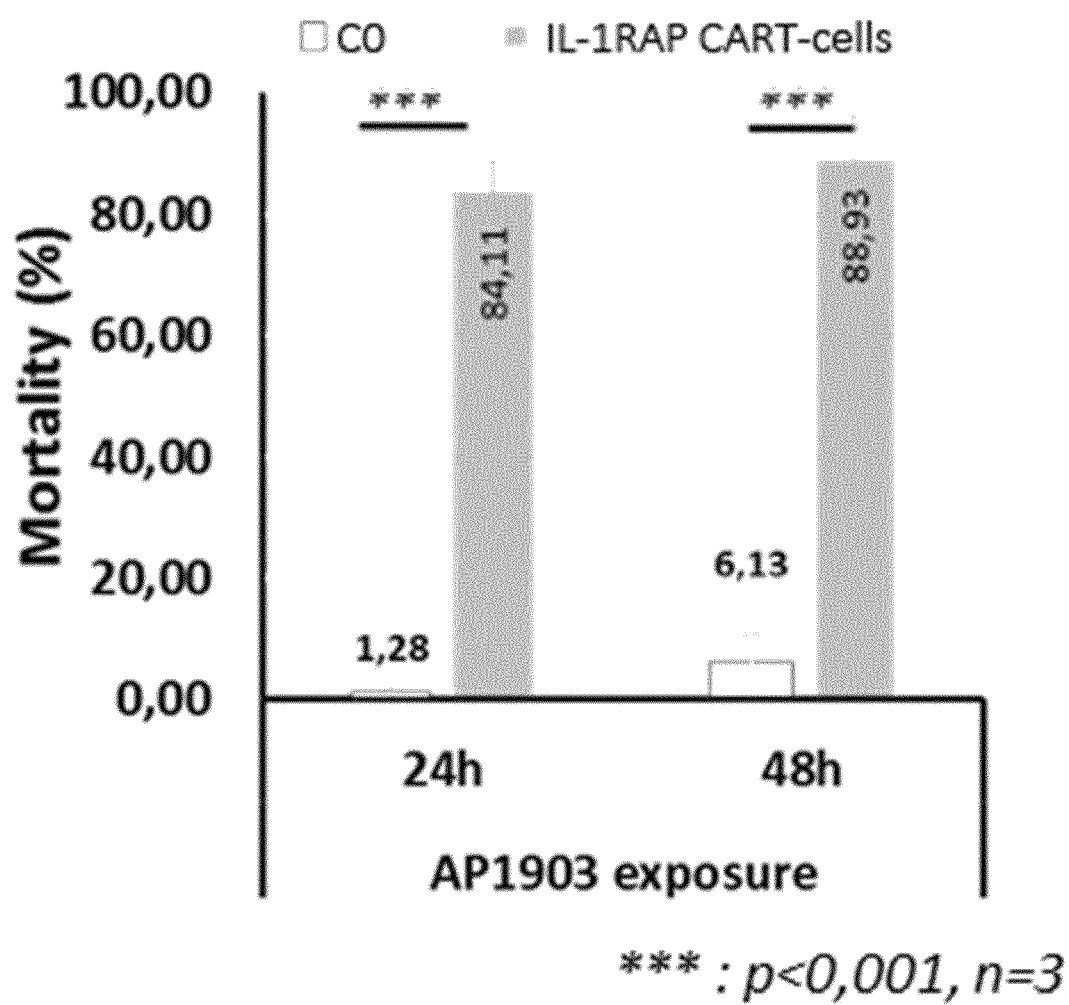
Figure 23G:
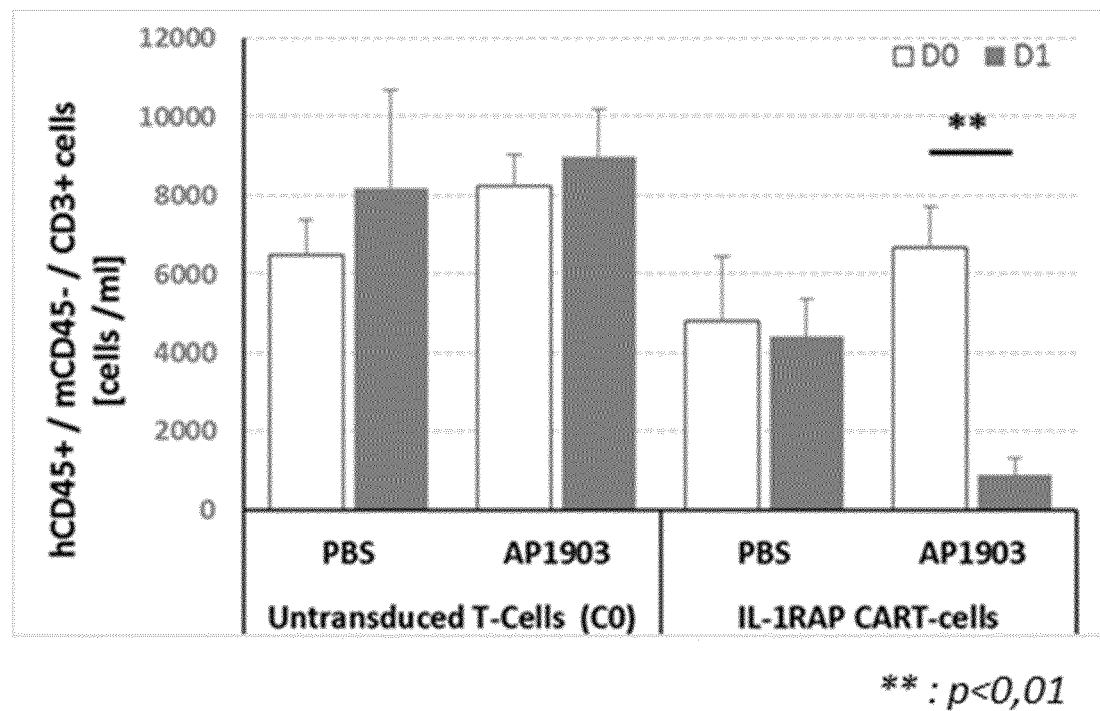

In order to limit the potential toxicity, we evaluated the functionality of the safety switch of the iCASP9/AP1903 suicide system cassette after exposure to chemical inducer dimerizer (CID; 10 nM). First, using optical microscopy, we noted that 293T cell culture transduced by IL-1RAP CAR was sensitive to the CID (FIG. 26, top). Cytometric analysis showed that, in a mixed population of CD19+ and CD19- IL-1RAP CART cells, only the CD19-CD3+ cells persisted after 24 hours of CID exposure (FIG. 26, bottom). More precisely, in a quantitative assay of apoptosis, 84.11% and 88.93% of IL-1RAP CART cells were eliminated after 24 hours or 48 hours of CID exposure, respectively, compared to non-transduced T cells (CO) (1.28% and 6.13% at 24 or 48 hours, respectively; p<0.001, n=3; FIG. 23F). Finally, in vivo evaluation of the safety switch in the NSG murine model showed that 87±7.32% (p<0.01, n=3) of IL-1RAP CART cells can be eliminated after i.p. AP1903 administration but were not affected after PBS administration, whereas control T cells (CO) are not affected by either treatment (FIG. 23G).

---

The invention claimed is:

1. An isolated nucleic acid molecule encoding a chimeric antigen receptor (CAR), wherein the CAR comprises an antibody or antibody fragment which includes an anti-IL-1RAP binding domain, a transmembrane domain, and an intracellular signaling domain comprising at least a stimulatory domain, and wherein said anti-IL-1RAP binding domain comprises:
(i) a light chain comprising a complementary determining region 1 (CDR1) comprising the amino acid sequence SEQ ID NO: 6, a complementary determining region 2 (CDR2) comprising the amino acid sequence SEQ ID NO: 7 and a complementary determining region 3 (CDR3) comprising the amino acid sequence SEQ ID NO: 8, and
(ii) a heavy chain comprising a complementary determining region 1 (CDR1) comprising the amino acid sequence SEQ ID NO: 12, a complementary determining region 2 (CDR2) comprising the amino acid sequence SEQ ID NO: 13 and a complementary determining region 3 (CDR3) comprising the amino acid sequence SEQ ID NO: 14.

2. The isolated nucleic acid molecule of claim 1, wherein the IL-1RAP binding domain is selected from the group consisting of an antibody, a Fv, a scFv, and a Fab.

3. The isolated nucleic acid molecule of claim 1, said transmembrane domain is a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154.

4. The isolated nucleic acid molecule of claim 1, wherein the anti-IL-1RAP binding domain is connected to the transmembrane domain by a hinge region.

5. The isolated nucleic acid molecule of claim 1, said intracellular signaling domain comprises at least one costimulatory domain selected from the group consisting of OX40, CD2, CD27, CD28, CDS, CD3 zeta, ICAM-1, LFA-1 (CD11a/CD18), ICOS (CD278), and 4-1BB (CD137).

6. The isolated nucleic acid of claim 2, wherein the IL-1RAP binding domain is a scFv.

7. The isolated nucleic acid of claim 3, wherein the transmembrane domain of a protein is CD28.

8. The isolated nucleic acid of claim 5, wherein the intracellular signaling domain comprises at least one 4-1 BB (CD137) costimulatory domain.

9. A vector comprising a nucleic acid molecule as defined in claim 1, wherein the vector is selected from the group consisting of a DNA, a RNA, a plasmid, a lentivirus vector, an adenoviral vector, and a retrovirus vector.

10. A cell comprising the vector of claim 9, wherein the cell is an immune effector cell.

11. The cell according to claim 10 wherein the immune effector cell expresses the CAR at its membrane.

12. The cell of claim 10, wherein the cell is a CD8+ T cell.

13. An isolated nucleic acid molecule encoding a chimeric antigen receptor (CAR), wherein the CAR comprises an antibody or antibody fragment which includes an anti-IL-1RAP binding domain, a CD28 transmembrane domain, and an intracellular signaling domain comprising the 4-1 BB (CD137) costimulatory domain,
wherein said anti-IL-1RAP binding domain comprises:
(i) a light chain comprising a complementary determining region 1 (CDR1) comprising the amino acid sequence SEQ ID NO: 6, a complementary determining region 2 (CDR2) comprising the amino acid sequence SEQ ID NO: 7 and a complementary determining region 3 (CDR3) comprising the amino acid sequence SEQ ID NO: 8, and
(ii) a heavy chain comprising a complementary determining region 1 (CDR1) comprising the amino acid sequence SEQ ID NO: 12, a complementary determining region 2 (CDR2) comprising the amino acid sequence SEQ ID NO: 13 and a complementary determining region 3 (CDR3) comprising the amino acid sequence SEQ ID NO: 14.

14. The isolated nucleic acid molecule of claim 13, wherein the anti-IL-1RAP binding domain comprises a heavy chain variable domain at least 90% identical to SEQ ID NO:2, and a light chain variable domain at least 90% identical to SEQ ID NO:4.

15. The isolated nucleic acid of claim 14, wherein the anti-IL-1RAP binding domain comprises the heavy chain variable domain of SEQ ID NO:2, and the light chain variable domain of SEQ ID NO:4.

16. The isolated nucleic acid molecule of claim 13, wherein: (i) the nucleic acid encoding the light chain CDR1 comprises SEQ ID NO: 9, the nucleic acid encoding the light chain CDR2 comprises SEQ ID NO: 10, the nucleic acid encoding the light chain CDR3 comprises SEQ ID NO: 11, and (ii) the nucleic acid encoding the heavy chain CDR1 comprises SEQ ID NO: 15, the nucleic acid encoding the heavy chain CDR2 comprises SEQ ID NO: 16, the nucleic acid encoding the heavy chain CDR3 comprises SEQ ID NO: 17.

17. The isolated nucleic acid of claim 13, wherein the nucleic acid encoding the heavy chain variable domain (VH) comprises SEQ ID NO:1; and the nucleic acid encoding the light chain variable domain (VL) comprises SEQ ID NO:3.

* * * * *

SEQUENCE LISTING

<160> NUMBER OF SEQ ID NOS: 18

<210> SEQ ID NO 1
<211> LENGTH: 423
<212> TYPE: DNA
<213> ORGANISM: Artificial Sequence
<220> FEATURE:
<223> OTHER INFORMATION: Nucleotide sequence coding chain H (VH) of
      murine scFv anti-IL-1RAP

<400> SEQUENCE: 1
atgggatgga gctgtatcat cctcttcttg gtagcaacag ctacaggtgt caactcccag      60
gtccaactgc agcagcctgg ggctgagctt atgatgcctg gggcttcagt gaaagtgtcc     120
tgcgaggctt ctggctacac attcactgac tcctggatgc actgggtgaa gcagaggcct     180
ggacaaggcc ttgagtggat cggagcgatt gatccttctg atagttatac tacctataat     240
caaaaattca cgggcaaggc cacattgagt gtagacgaat cctccaacac agcctacatg     300
cagctcagca gcctgacatc tgaggactct gcggtctatt actgtgcaag gtattactcc     360
ggtagtaact acatatcgcc ctttccttac tggggccaag ggactctggt cactgtctct     420
gca                                                                   423

<210> SEQ ID NO 2
<211> LENGTH: 141
<212> TYPE: PRT
<213> ORGANISM: Artificial Sequence
<220> FEATURE:
<223> OTHER INFORMATION: Amino acid sequence of chain H (VH) of murine
      scFv anti-IL-1RAP

<400> SEQUENCE: 2

Met Gly Trp Ser Cys Ile Ile Leu Phe Leu Val Ala Thr Ala Thr Gly
1               5                   10                  15

Val Asn Ser Gln Val Gln Leu Gln Gln Pro Gly Ala Glu Leu Met Met
            20                  25                  30

Pro Gly Ala Ser Val Lys Val Ser Cys Glu Ala Ser Gly Tyr Thr Phe
        35                  40                  45

Thr Asp Ser Trp Met His Trp Val Lys Gln Arg Pro Gly Gln Gly Leu
    50                  55                  60

Glu Trp Ile Gly Ala Ile Asp Pro Ser Asp Ser Tyr Thr Thr Tyr Asn
65                  70                  75                  80

Gln Lys Phe Thr Gly Lys Ala Thr Leu Ser Val Asp Glu Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Ser Gly Ser Asn Tyr Ile Ser Pro Phe

```
              115                 120                 125

Pro Tyr Trp Gly Gln Gly Thr Leu Val Thr Val Ser Ala
    130                 135                 140

<210> SEQ ID NO 3
<211> LENGTH: 382
<212> TYPE: DNA
<213> ORGANISM: Artificial Sequence
<220> FEATURE:
<223> OTHER INFORMATION: Nucleotide sequence coding chain K (VL) of
      murine scFv anti-IL-1RAP

<400> SEQUENCE: 3
atggagtcac agattcaggt ctttgtattc gtgtttctct ggttgtctgg tgttgacgga      60
gacattgtga tgacccagtc tcacaaattc atgtccacat cagtaggaga cagggtcacc    120
atcacctgca aggccagtct ggatgtgagt actgctgtgg cctggtatca acagaaacca    180
ggacaatctc ctaaactact gatttactcg gcatcctacc ggtacactgg agtccctgat    240
cgcttcactg gcagtggatc tgggacggat ttcactttca ccatcagcag tgtgcaggct    300
gaagacctgg cagtttatta ctgtcagcaa cattatagtc ctccattcac gttcggctcg    360
gggacaaact tggagataaa ac                                             382

<210> SEQ ID NO 4
<211> LENGTH: 127
<212> TYPE: PRT
<213> ORGANISM: Artificial Sequence
<220> FEATURE:
<223> OTHER INFORMATION: Amino acid sequence of chain K (VL) of murine
      scFv anti-IL-1RAP

<400> SEQUENCE: 4

Met Glu Ser Gln Ile Gln Val Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Thr Ile Thr Cys Lys Ala Ser Leu Asp
        35                  40                  45

Val Ser Thr Ala Val Ala Trp Tyr Gln Gln Lys Pro Gly Gln Ser Pro
    50                  55                  60

Lys Leu Leu Ile Tyr Ser Ala Ser Tyr Arg Tyr Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Tyr Cys Gln Gln His Tyr
            100                 105                 110

Ser Pro Pro Phe Thr Phe Gly Ser Gly Thr Asn Leu Glu Ile Lys
        115                 120                 125

<210> SEQ ID NO 5
<211> LENGTH: 15
<212> TYPE: PRT
<213> ORGANISM: Artificial Sequence
<220> FEATURE:
<223> OTHER INFORMATION: Linker between the VH and VL domains

<400> SEQUENCE: 5

Gly Gly Ser Gly Gly Gly Gly Ser Gly Gly Gly Gly Ser Val Asp
1               5                   10                  15
```

```
<210> SEQ ID NO 6
<211> LENGTH: 6
<212> TYPE: PRT
<213> ORGANISM: Artificial Sequence
<220> FEATURE:
<223> OTHER INFORMATION: CDR1 of the light chain

<400> SEQUENCE: 6

Leu Asp Val Ser Thr Ala
1               5

<210> SEQ ID NO 7
<211> LENGTH: 3
<212> TYPE: PRT
<213> ORGANISM: Artificial Sequence
<220> FEATURE:
<223> OTHER INFORMATION: CDR2 of the light chain

<400> SEQUENCE: 7

Ser Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: CDR3 of the light chain

<400> SEQUENCE: 8

Gln Gln His Tyr Ser Pro Pro Phe Thr
1               5

<210> SEQ ID NO 9
<211> LENGTH: 18
<212> TYPE: DNA
<213> ORGANISM: Artificial Sequence
<220> FEATURE:
<223> OTHER INFORMATION: CDR1 of the light chain (nt)

<400> SEQUENCE: 9
ctggatgtga gtactgct                                                 18

<210> SEQ ID NO 10
<211> LENGTH: 9
<212> TYPE: DNA
<213> ORGANISM: Artificial Sequence
<220> FEATURE:
<223> OTHER INFORMATION: CDR2 of the light chain (nt)

<400> SEQUENCE: 10 tcggcatcc                                                            9

<210> SEQ ID NO 11
<211> LENGTH: 27
<212> TYPE: DNA
<213> ORGANISM: Artificial Sequence
<220> FEATURE:
<223> OTHER INFORMATION: CDR3 of the light chain (nt)

<400> SEQUENCE: 11
cagcaacatt atagtcctcc attcacg                                       27

<210> SEQ ID NO 12
<211> LENGTH: 8
<212> TYPE: PRT
<213> ORGANISM: Artificial Sequence
```

```
<220> FEATURE:
<223> OTHER INFORMATION: CDR1 of the heavy chain

<400> SEQUENCE: 12

Gly Tyr Thr Phe Thr Asp Ser Trp
1               5

<210> SEQ ID NO 13
<211> LENGTH: 8
<212> TYPE: PRT
<213> ORGANISM: Artificial Sequence
<220> FEATURE:
<223> OTHER INFORMATION: CDR2 of the heavy chain

<400> SEQUENCE: 13

Ile Asp Pro Ser Asp Ser Tyr Thr
1               5

<210> SEQ ID NO 14
<211> LENGTH: 15
<212> TYPE: PRT
<213> ORGANISM: Artificial Sequence
<220> FEATURE:
<223> OTHER INFORMATION: CDR3 of the heavy chain

<400> SEQUENCE: 14

Ala Arg Tyr Tyr Ser Gly Ser Asn Tyr Ile Ser Pro Phe Pro Tyr
1               5                   10                  15

<210> SEQ ID NO 15
<211> LENGTH: 24
<212> TYPE: DNA
<213> ORGANISM: Artificial Sequence
<220> FEATURE:
<223> OTHER INFORMATION: CDR1 of the heavy chain (nt)

<400> SEQUENCE: 15
ggctacacat tcactgactc ctgg                                      24

<210> SEQ ID NO 16
<211> LENGTH: 24
<212> TYPE: DNA
<213> ORGANISM: Artificial Sequence
<220> FEATURE:
<223> OTHER INFORMATION: CDR2 of the heavy chain (nt)

<400> SEQUENCE: 16
attgatcctt ctgatagtta tact                                      24

<210> SEQ ID NO 17
<211> LENGTH: 45
<212> TYPE: DNA
<213> ORGANISM: Artificial Sequence
<220> FEATURE:
<223> OTHER INFORMATION: CDR3 of the heavy chain (nt)

<400> SEQUENCE: 17
gcaaggtatt actccggtag taactacata tcgccctttc cttac               45

<210> SEQ ID NO 18
<211> LENGTH: 283
<212> TYPE: PRT
<213> ORGANISM: Artificial Sequence
<220> FEATURE:
<223> OTHER INFORMATION: Amino acid sequence of murine scFv anti-IL-1RAP
      (i.e. #A3C3 CAR)
```

```
<400> SEQUENCE: 18

Met Gly Trp Ser Cys Ile Ile Leu Phe Leu Val Ala Thr Ala Thr Gly
1               5                   10                  15

Val Asn Ser Gln Val Gln Leu Gln Gln Pro Gly Ala Glu Leu Met Met
            20                  25                  30

Pro Gly Ala Ser Val Lys Val Ser Cys Glu Ala Ser Gly Tyr Thr Phe
        35                  40                  45

Thr Asp Ser Trp Met His Trp Val Lys Gln Arg Pro Gly Gln Gly Leu
    50                  55                  60

Glu Trp Ile Gly Ala Ile Asp Pro Ser Asp Ser Tyr Thr Thr Tyr Asn
65                  70                  75                  80

Gln Lys Phe Thr Gly Lys Ala Thr Leu Ser Val Asp Glu Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Ser Gly Ser Asn Tyr Ile Ser Pro Phe
        115                 120                 125

Pro Tyr Trp Gly Gln Gly Thr Leu Val Thr Val Ser Ala Gly Gly Ser
    130                 135                 140

Gly Gly Gly Gly Ser Gly Gly Gly Ser Val Asp Met Glu Ser Gln
145                 150                 155                 160

Ile Gln Val Phe Val Phe Val Phe Leu Trp Leu Ser Gly Val Asp Gly
                165                 170                 175

Asp Ile Val Met Thr Gln Ser His Lys Phe Met Ser Thr Ser Val Gly
            180                 185                 190

Asp Arg Val Thr Ile Thr Cys Lys Ala Ser Leu Asp Val Ser Thr Ala
        195                 200                 205

Val Ala Trp Tyr Gln Gln Lys Pro Gly Gln Ser Pro Lys Leu Leu Ile
    210                 215                 220

Tyr Ser Ala Ser Tyr Arg Tyr Thr Gly Val Pro Asp Arg Phe Thr Gly
225                 230                 235                 240

Ser Gly Ser Gly Thr Asp Phe Thr Phe Thr Ile Ser Ser Val Gln Ala
                245                 250                 255

Glu Asp Leu Ala Val Tyr Tyr Cys Gln Gln His Tyr Ser Pro Pro Phe
            260                 265                 270

Thr Phe Gly Ser Gly Thr Asn Leu Glu Ile Lys
        275                 280
```